US011211156B2

(12) United States Patent
Iyer et al.

(10) Patent No.: US 11,211,156 B2
(45) Date of Patent: Dec. 28, 2021

(54) DIGITAL THERAPEUTIC SYSTEMS AND METHODS

(71) Applicant: Welldoc, Inc., Columbia, MD (US)

(72) Inventors: Anand Iyer, Columbia, MD (US);
Malinda Peeples, Columbia, MD (US);
Vinayak Shenoy, Columbia, MD (US);
Carey Hutchins, Columbia, MD (US)

(73) Assignee: Welldoc, Inc., Columbia, MD (US)

( * ) Notice: Subject to any disclaimer, the term of this patent is extended or adjusted under 35 U.S.C. 154(b) by 0 days.

(21) Appl. No.: 17/177,695

(22) Filed: Feb. 17, 2021

(65) Prior Publication Data

US 2021/0174924 A1 Jun. 10, 2021

Related U.S. Application Data

(63) Continuation of application No. PCT/US2020/063474, filed on Dec. 4, 2020.

(60) Provisional application No. 62/943,536, filed on Dec. 4, 2019.

(51) Int. Cl.
*G16H 50/30* (2018.01)
*G16H 15/00* (2018.01)
*G06N 20/00* (2019.01)
*G16H 20/00* (2018.01)
*A61B 5/00* (2006.01)

(52) U.S. Cl.
CPC .............. *G16H 15/00* (2018.01); *G06N 20/00* (2019.01); *G16H 20/00* (2018.01)

(58) Field of Classification Search
CPC ........ G16H 15/00; G16H 20/00; G16H 20/70; G16H 50/20; G16H 20/10; G16H 50/30; G16H 80/00; G06N 20/00; A61B 5/00; A61B 5/16; G06F 19/00; G06F 19/322; G09B 7/06; G09B 19/00
USPC .......................................................... 705/2, 3
See application file for complete search history.

(56) References Cited

U.S. PATENT DOCUMENTS

| 6,256,613 | B1 | 7/2001 | Falchuk et al. |
| 7,935,307 | B2 | 5/2011 | Angelides |
| 8,568,309 | B2 | 10/2013 | Angelides |
| 8,812,244 | B2 | 8/2014 | Angelides |
| 10,595,754 | B2 | 3/2020 | Pushpala et al. |

(Continued)

FOREIGN PATENT DOCUMENTS

| AU | 2019335192 A1 | 4/2021 |
| AU | 2019376487 A1 | 5/2021 |

(Continued)

OTHER PUBLICATIONS

International Search Report and Written Opinion issued in International Application No. PCT/US2020/063474, dated Feb. 11, 2021, (15 pages).

*Primary Examiner* — Jonathan Durant
*Assistant Examiner* — Alaaeldin M Elshaer
(74) *Attorney, Agent, or Firm* — Bookoff McAndrews, PLLC

(57) ABSTRACT

Methods and devices include identifying a plurality of target users for the digital therapeutic based on one or more target parameters, conducting outreach to one or more of the plurality of target users using an outreach medium, identifying an activation mechanism to optimize use of the digital therapeutic, and encouraging an engagement level of the digital therapeutic by one or more of the plurality of target users.

17 Claims, 9 Drawing Sheets

(56) References Cited

U.S. PATENT DOCUMENTS

| | | |
|---|---|---|
| 2003/0208113 A1 | 11/2003 | Mault et al. |
| 2010/0222649 A1* | 9/2010 | Schoenberg ........... G16H 40/67 600/301 |
| 2013/0117040 A1 | 5/2013 | James et al. |
| 2014/0222454 A1 | 8/2014 | Duffy et al. |
| 2015/0079561 A1 | 3/2015 | Petakov et al. |
| 2016/0029931 A1 | 2/2016 | Salas-Boni et al. |
| 2016/0029966 A1 | 2/2016 | Salas-Boni et al. |
| 2017/0061091 A1* | 3/2017 | McElhinney .......... G16H 10/60 |
| 2017/0076630 A1 | 3/2017 | Angelides et al. |
| 2017/0329917 A1 | 11/2017 | McRaith et al. |
| 2018/0315495 A1* | 11/2018 | Chekroud .............. G16H 80/00 |
| 2019/0074080 A1 | 3/2019 | Appelbaum et al. |
| 2019/0240430 A1 | 8/2019 | Jackson et al. |
| 2020/0375549 A1 | 12/2020 | Wexler et al. |
| 2020/0383648 A1 | 12/2020 | Bridgewater et al. |
| 2020/0388393 A1 | 12/2020 | Boulos et al. |
| 2020/0388403 A1 | 12/2020 | Boulos et al. |
| 2021/0128833 A1 | 5/2021 | Debong et al. |

FOREIGN PATENT DOCUMENTS

| | | | |
|---|---|---|---|
| CA | 3105740 A1 | 1/2020 | |
| CA | 3111924 A1 | 3/2020 | |
| CN | 107845418 A | 3/2018 | |
| CN | 112655045 A | 4/2021 | |
| EP | 3651164 A1 | 5/2020 | |
| IN | 202147020470 A | 5/2021 | |
| JP | 2018032438 A | 3/2018 | |
| JP | 2020091885 A | 6/2020 | |
| WO | 2015153127 A1 | 10/2015 | |
| WO | 2020094765 A1 | 5/2020 | |
| WO | WO-2020198065 A1 * | 10/2020 | ............ G16H 50/20 |
| WO | 2020243576 A1 | 12/2020 | |
| WO | 2020247032 A1 | 12/2020 | |

\* cited by examiner

DIGITAL THERAPEUTIC SYSTEMS AND METHODS

CROSS-REFERENCE TO RELATED APPLICATIONS

This application is a continuation of and claims the benefit of priority to Application No. PCT/US2020/063474, filed Dec. 4, 2020, which claims the benefit of U.S. Provisional Application No. 62/943,536, filed Dec. 4, 2019, the entireties of each of which are incorporated by reference herein.

TECHNICAL FIELD

The present disclosure relates generally to obtaining and processing data to implement a digital therapeutic system adapted to improve the health of a user.

INTRODUCTION

Increased healthcare costs have limited patient access to appropriate care. At the same time, healthcare companies have increased provider workloads and limited physician-patient interactions. Digital therapeutics can offer a reduction in cost and a novel treatment implementation. However, digital therapeutics have yet to achieve critical mass due to a lack of a standardized value chain, lack of key processes, lack of metrics, and lack of best practices and benchmarking.

The present disclosure is directed to addressing one or more of the above-referenced challenges. The introduction provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

This disclosure is directed to a computer-implemented method for deploying a digital therapeutic including identifying a plurality of target users for the digital therapeutic based on one or more target parameters, conducting outreach to one or more of the plurality of target users using an outreach medium, identifying an activation mechanism to optimize use of the digital therapeutic, and encouraging an engagement level of the digital therapeutic by one or more of the plurality of target users.

Techniques disclosed include generating a report based on one or more of the target users, the outreach, the activation mechanism, or the engagement level. The report may be based on one or more of an informative analysis, discovery analysis, extrapolative analysis, or an adaptive analysis. The report may include a comparison of an N+1 stage score to an N stage score.

The plurality of target users are identified based on one or more of clinical factors, disease factors, technology factors, social factors, or demographic factors. The outreach is conducted based on one or more of a method, a modality, a frequency, a time, or a level of interaction. The activation mechanism is based on one or more of a modality, data-enablement verses data-entry, or a location. The engagement level is based on one or more of an in-solution versus out-of-solution, a frequency, a length, and a modality. At least one of the identifying the plurality of target users, conducting outreach, identifying an activation mechanism, and encouraging an engagement level is based on an output of a machine learning model. The machine learning model is trained my modifying one of one or more weights or one or more layers based on training data. The training data comprises one or more of stage inputs, known outcomes, and comparison results. The comparison results are a ratio of an N+1 stage score to an N stage score.

BRIEF DESCRIPTION OF THE DRAWINGS

The accompanying drawings, which are incorporated in and constitute a part of this specification, illustrate examples of the disclosure and together with the description, serve to explain the principles of the disclosure.

DETAILED DESCRIPTION

Reference will now be made in detail to examples of the disclosure, which are illustrated in the accompanying drawings. Wherever possible, the same reference numbers will be used throughout the drawings to refer to the same or like parts.

In the discussion that follows, relative terms such as "about," "substantially," "approximately," etc. are used to indicate a possible variation of ±10% in a stated numeric value. It should be noted that the description set forth herein is merely illustrative in nature and is not intended to limit the examples of the subject matter, or the application and uses of such examples. Any implementation described herein as exemplary is not to be construed as preferred or advantageous over other implementations. Rather, as alluded to above, the term "exemplary" is used in the sense of example or "illustrative," rather than "ideal." The terms "comprise," "include," "have," "with," and any variations thereof are used synonymously to denote or describe a non-exclusive inclusion. As such, a process, method, article, or apparatus that uses such terms does not include only those steps, structure or elements but may include other steps, structures or elements not expressly listed or inherent to such process, method, article, or apparatus. Further, the terms "first," "second," and the like, herein do not denote any order, quantity, or importance, but rather are used to distinguish one element from another. Moreover, the terms "a" and "an" herein do not denote a limitation of quantity, but rather denote the presence of at least one of the referenced item.

Healthcare and Computing Environment

Figure 1:
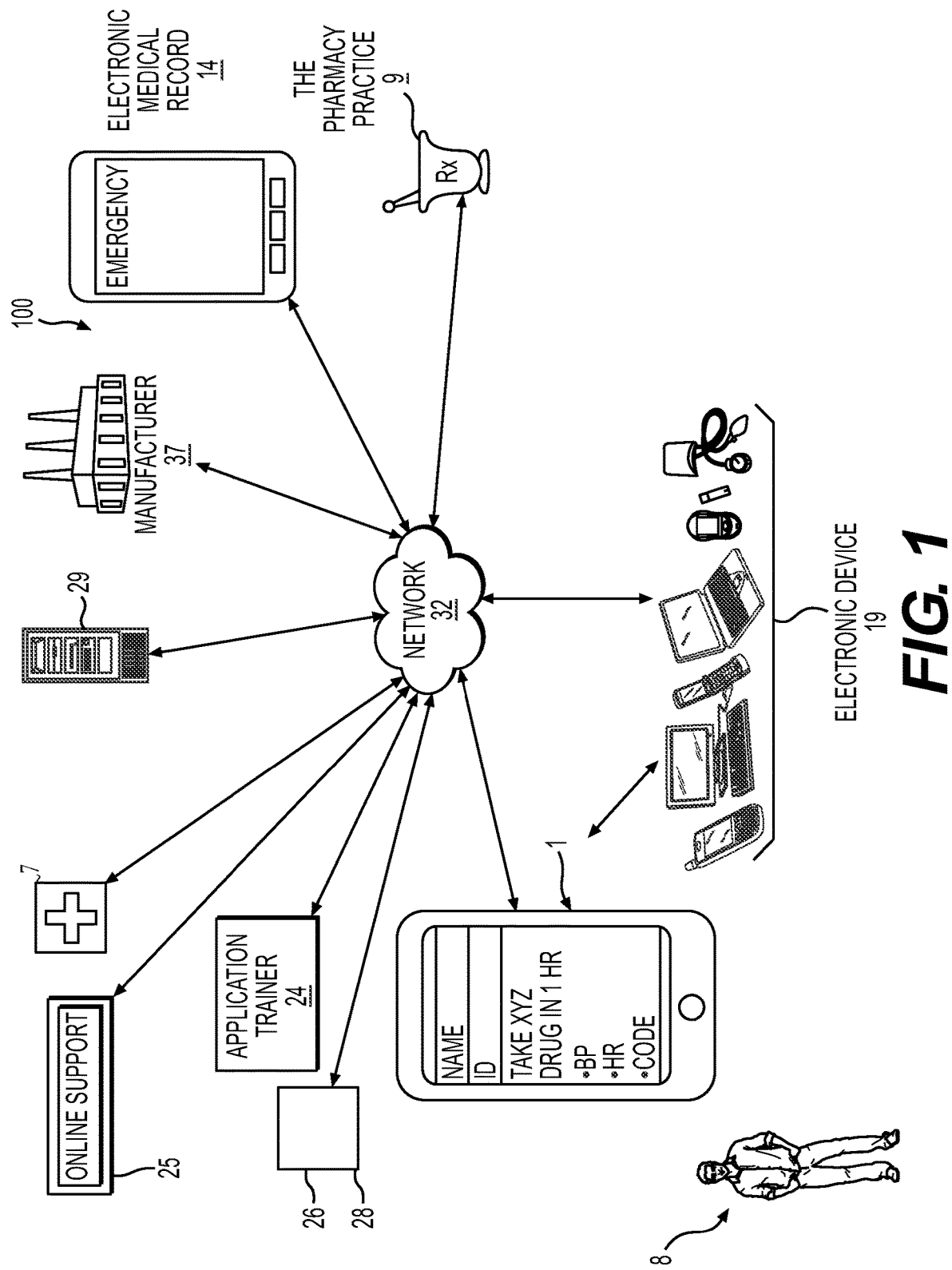
FIG. 1 is a schematic illustration of a health management system, according to an example of the present disclosure.

FIG. 1 is a block diagram of a health management system 100, according to an example of the present disclosure. A user (e.g., a patient, consumer, or the like) 8 having an electronic device 19, such as a mobile device, computer, medical device, or any other electronic device configured to access an electronic network 32, such as the Internet, may communicate with or otherwise access a mobile health (mHealth) application 1. The mHealth application 1 is an example of a digital therapeutic, as further disclosed herein. According to some examples, network 32 may include wireless or wired links, such as mobile telephone networks, Wi-Fi, LANs, WANs, Bluetooth, near-field communication (NFC), or other suitable forms of network communication. Multiple electronic devices 19 may be configured to access electronic network 32. A user 8 may access mHealth application 1 with a single account linked to multiple electronic devices 19 (e.g., via one or more of a mobile phone, a tablet, and a laptop computer). Electronic device 19 also may include, but is not limited to, mobile health devices, a desktop computer or workstation, a laptop computer, a mobile handset, a personal digital assistant (PDA), a cellular telephone, a network appliance, a camera, a smart phone, a smart watch, an enhanced general packet radio service (EGPRS) mobile phone, a media player, a navigation device, a game console, a set-top box, a biometric sensing device with communication capabilities, a smart TV, or any combination of these or other types of computing devices having at least one processor, a local memory, a display (e.g., a monitor or touchscreen display), one or more user input devices, and a network communication interface. The electronic device 19 may include any type or combination of input/output devices, such as a display monitor, keyboard, touchpad, accelerometer, gyroscope, mouse, touchscreen, camera, a projector, a touch panel, a pointing device, a scrolling device, a button, a switch, a motion sensor, an audio sensor, a pressure sensor, a thermal sensor, and/or microphone. Electronic devices 19 also may communicate with each other by any suitable wired or wireless means (e.g., via Wi-Fi, radio frequency (RF), infrared (IR), Bluetooth, Near Field Communication, or any other suitable means) to send and receive information.

mHealth application 1 may be in communication with other entities or networks to send and receive information. In some examples, mHealth application 1 may communicate with one or more applications associated with the user 8 such as, e.g., exercise tracking (e.g., step tracking) applications and/or other health-related applications. mHealth application 1 may be able to import data from the other applications to analyze and use in generating treatment plans for the user 8. For example, mHealth application 1 may import activity tracking data from another application and use that data to identify patterns between user 8 exercise and blood glucose values collected prior to the use of mHealth application 1. mHealth application 1 also may import any other suitable data from other mobile health applications such as, e.g., blood pressure, BMI, A1C, exercise type, exercise duration, exercise distance, calories burned, total steps, exercise date, exercise start and stop times, and sleep. mHealth application 1 also may export data to other mobile applications, including, e.g., other mobile health applications having social or interactive features. A healthcare provider 7, such as a physician, may prescribe the application. However, it is also contemplated that mHealth application 1 may not require a prescription, e.g., that it may be a commercially available consumer application accessible without a prescription from a digital distribution platform for computer software. mHealth application 1 may be tailored to a specific user 8 and may be activated in person by the user 8 by visiting a pharmacy 9 or other authorized entity. For example, the user 8 may receive an access code from the pharmacy that authorizes access to mHealth application 1. The user 8 may receive training on using mHealth application 1 by a mHealth support system 25 and/or application trainer 24. mHealth application 1 may include programming 28 of various forms, such as machine learning programming algorithms 26. The user treatment plan may include a prescription (e.g., for a drug, device, and/or therapy), which may be dispensed by the pharmacy 9. The pharmacy 9 may allow the refill of the prescribed product/therapy after receiving authorization based on the user's compliance with his/her healthcare treatment plan. The authorization may be received by the pharmacy 9 by a communication from the application 1, via, e.g., the network 32 and various servers 29. Use of the drug or other medical product/therapy also may be sent to the manufacturer 37 over the network 32 to inform the manufacturer 37 of the amount of medical product or therapy being used by user 8. This information may assist the manufacturer 37 in assessing demand and planning supply of the medical product or therapy. The healthcare provider 7 also may receive a report based on the user information received by the application 1, and may update the user treatment plan based on this information. The user's electronic medical record 14 also may be automatically updated via the network 32 based on the user information, which may include electronically transmitted user 8 feedback on the application, received by mHealth application 1. Healthcare provider 7 may be any suitable healthcare provider including, e.g., a doctor, specialist, nurse, educator, social worker, MA, PA, or the like.

Figure 2:
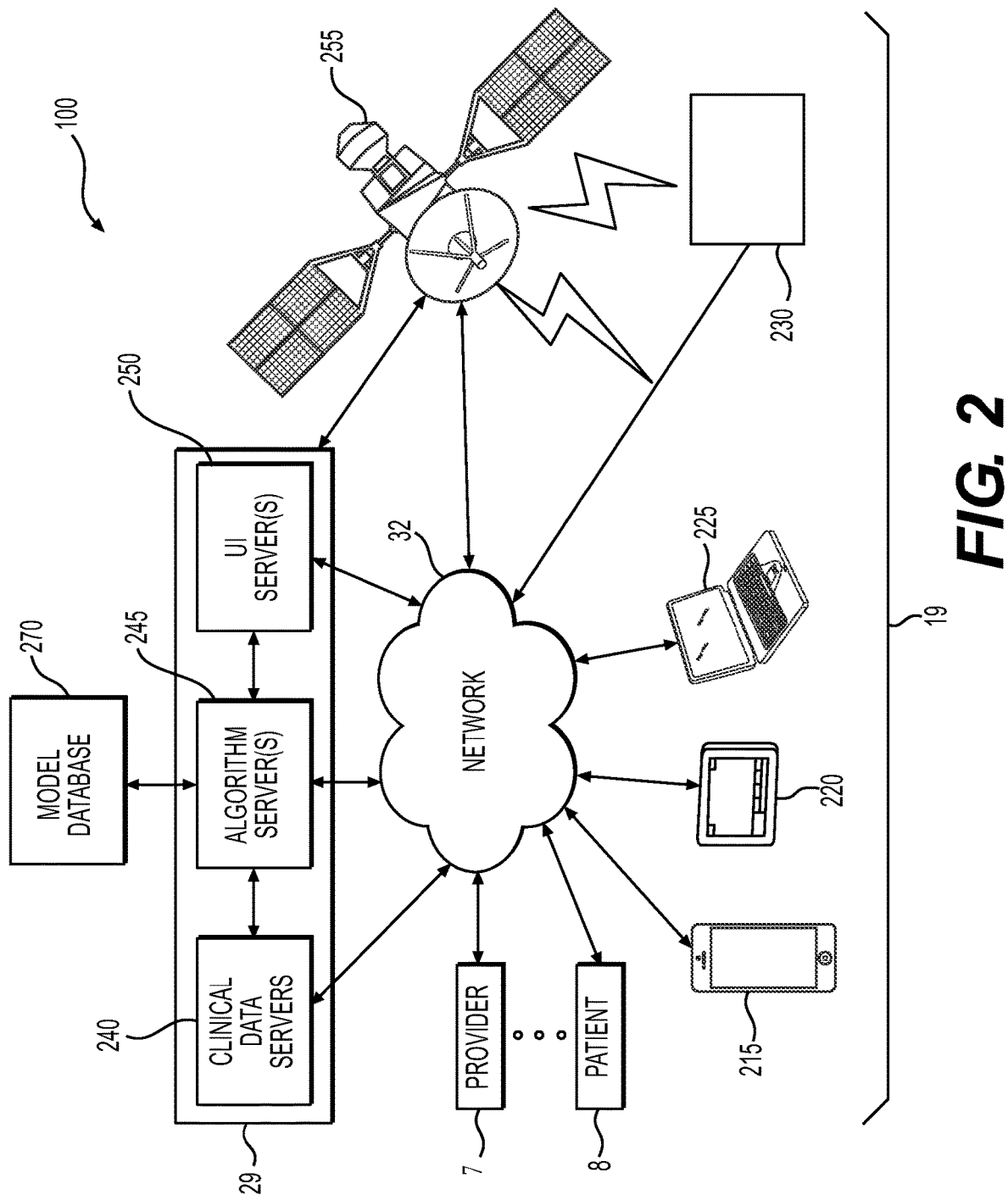
FIG. 2 is a schematic illustration of a portion of the health management system of FIG. 1.

FIG. 2 is a schematic diagram of additional aspects of system 100. For example, the system 100 may access decision models stored on a decision model database 270 via network 32. The retrieved decision models may be used for display and/or processing by one or more electronic devices 19, such as a mobile device 215, a tablet device 220, a computer (e.g., a laptop or desktop) 225, a kiosk 230 (e.g., at a kiosk, pharmacy, clinic, or hospital having medical and/or prescription information), and/or any device connected to network 32.

In the example shown in FIG. 2, mobile device 215, tablet 220, and computer 225 each may be equipped with or include, for example, a GPS receiver for obtaining and reporting location information, e.g., GPS data, via network 32 to and from any of servers 29 and/or one or more GPS satellites 255.

Each of electronic devices 19, including mobile device 215, tablet device 220, computer 225, and/or kiosk 230, may be configured to send and receive data (e.g., clinical information) to and from a system of servers 29 over network 32. Each of devices 19 may receive information, such as clinical data via the network 32 from servers 29. Servers 29 may include clinical data servers 240, algorithm servers 245, user interface (UI) servers 250, and/or any other suitable servers. Electronic device 19 may include a user interface that is in data communication with UI server 250 via network 32. Each server may access the decision model database 270 to retrieve decision models. Each server may include memory, a processor, and/or a database. For example, the clinical data server 240 may have a processor configured to retrieve clinical data from a provider's database and/or a patient's electronic medical record. The algorithm server 245 may have a database that includes various algorithms, and a processor configured to process the clinical data. The UI server 250 may be configured to receive and process user 8 input, such as clinical decision preferences. The satellite 255 may be configured to send and receive information between servers 29 and devices 19.

The clinical data server 240 may receive clinical data, such as data regarding the user from the electronic device 19 via the network 32 or indirectly via the UI server 250. The clinical data server 240 may save the information in memory, such as a computer readable memory.

The clinical data server 240 also may be in communication with one or more other servers, such as the algorithm server 245 and/or external servers. The servers 29 may include data about provider preferences, and/or user 8 health history. In addition, the clinical data server 240 may include data from other users. The algorithm server 245 may include machine learning, and/or other suitable algorithms. The algorithm server 245 also may be in communication with other external servers and may be updated as desired. For example, the algorithm server 245 may be updated with new algorithms, more powerful programming, and/or more data. The clinical data server 240 and/or the algorithm server 245 may process the information and transmit data to the model database 270 for processing. In one example, algorithm server(s) 245 may be obtain a pattern definition in a simple format, predict several time steps in the future by using models ,e.g., Markov models, Gaussian, Bayesian, and/or classification models such as linear discriminant functions, nonlinear discriminant functions, random forest algorithms and the like, optimize results based on its predictions, detect transition between patterns, obtain abstract data and extract information to infer higher levels of knowledge, combine higher and lower levels of information to understand about the user 8 and clinical behaviors, infer from multi-temporal (e.g., different time scales) data and associated information, use variable order Markov models, and/or reduce noise over time by employing clustering algorithms, such as k-means clustering.

Each server in the system of servers 29, including clinical data server 240, algorithm server 245, and UI server 250, may represent any of various types of servers including, but not limited to, a web server, an application server, a proxy server, a network server, or a server farm. Each server in the system of servers 29 may be implemented using, for example, any general-purpose computer capable of serving data to other computing devices including, but not limited to, devices 19 or any other computing device (not shown) via network 32. Such a general-purpose computer can include, but is not limited to, a server device having a processor and memory for executing and storing instructions. The memory may include any type of random access memory (RAM) or read-only memory (ROM) embodied in a physical storage medium, such as magnetic storage including floppy disk, hard disk, or magnetic tape; semiconductor storage such as solid-state disk (SSD) or flash memory; optical disc storage; or magneto-optical disc storage. Software may include one or more applications and an operating system. Hardware can include, but is not limited to, a processor, memory, and graphical UI display. Each server also may have multiple processors and multiple shared or separate memory components that are configured to function together within, for example, a clustered computing environment or server farm.

Figure 3:
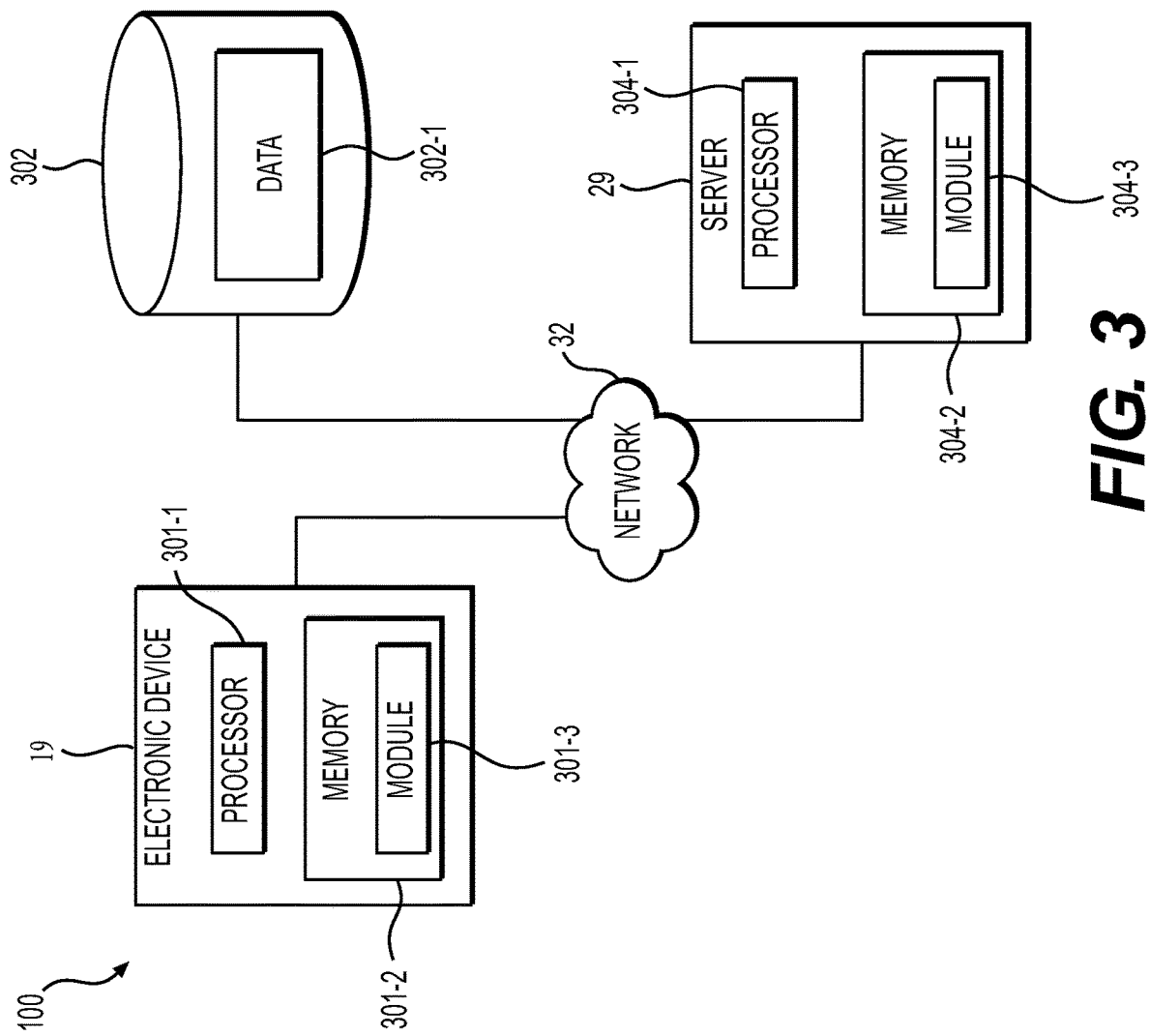
FIG. 3 is a schematic illustration of another portion of the health management system of FIG. 1.

FIG. 3 is another representation of a portion of system 100 showing additional details of electronic device 19 and a server 29. Electronic device 19 and server 29 each may contain one or more processors, such as processors 301-1 and 304-1. Processors 301-1 and 304-1 each may be a central processing unit, a microprocessor, a general purpose processor, an application specific processor, or any device that executes instructions. Electronic device 19 and server 29 also may include one or more memories, such as memories 301-2 and 304-2, that store one or more software modules. Memories 301-2 and 304-2 may be implemented using any computer-readable storage medium, such as hard drives, CDs, DVDs, flash memory, RAM, ROM, etc. Memory 301-2 may store a module 301-3, which may be executed by processor 301-1. Similarly, memory 304-2 may store a module 304-3, which may be executed by processor 304-1.

Electronic device 19 may further comprise one or more UIs. The UI may allow one or more interfaces to present information to a user 8, such as a plan or intervention. The UI may be web based, such as a web page, or a stand-alone application. The UI also may be configured to accept information about a user 8, such as data inputs and user feedback. The user 8 may manually enter the information, or it may be entered automatically. In an example, the user 8 (or the user's caretaker) may enter information such as when medication was taken or what food and drink the user 8 consumed. Electronic device 19 also may include testing equipment (not shown) or an interface for receiving information from testing equipment. Testing equipment may include, for example, a blood glucose meter, heart rate monitor, weight scale, blood pressure cuff, or the like. The electronic device 19 also may include one or more sensors (not shown), such as a camera, microphone, or accelerometer, for collecting feedback from a user 8. In one example, the device may include a glucose meter for reading and automatically reporting the user's blood glucose levels.

Electronic device 19 also may include a presentation layer. The presentation layer may be a web browser, application, messaging interface (e.g., e-mail, instant message, SMS, etc.), etc. The electronic device 19 may present notifications, alerts, reading materials, references, guides, reminders, or suggestions to a user 8 via presentation layer. For example, the presentation layer may present articles that are determined to be relevant to the user 8, reminders to purchase medications, tutorials on topics (e.g., a tutorial on carbohydrates), testimonials from others with similar symptoms, and/or one or more goals (e.g., a carbohydrate counting goal). The presentation layer also may present information such as a tutorial (e.g., a user guide or instructional video) and/or enable communications between the healthcare provider, and the user 8, e.g., patient. The communications between the healthcare provider, and the user 8, e.g., patient, may be via electronic messaging (e.g., e-mail or SMS), voice, or real-time video. One or more of these items may be presented based on a treatment plan or an updated treatment plan, as described later. The presentation layer also may be used to receive feedback from a user.

The system 100 also may include one or more databases, such as a database 302. Database 302 may be implemented using any database technology known to one of ordinary skill in the art, such as relational database technology or object-oriented database technology. Database 302 may store data 302-1. Data 302-1 may include a knowledge base for making inferences, statistical models, and/or user information. Data 302-1, or portions thereof, may be alternatively or simultaneously stored in server 29 or electronic device 19.

System 100 can be used for a wide range of applications, including, for example, addressing a user's healthcare, maintaining a user's finances, and monitoring and tracking a user's nutrition and/or sleep. In some implementations of system 100, any received data may be stored in the databases in an encrypted form to increase security of the data against unauthorized access and complying with HIPAA privacy, and/or other legal, healthcare, financial, or other regulations.

For any server or server systems 29 depicted in system 100, the server or server system may include one or more databases. In an example, databases may be any type of data store or recording medium that may be used to store any type of data. For example, database 302 may store data received by or processed by server 29 including information related to a user's treatment plan, including timings and dosages associated with each prescribed medication of a treatment plan. Database 302 also may store information related to the user 8 including their literacy level related to each of a plurality of prescribed medications.

Health Conditions

Diabetes mellitus (commonly referred to as diabetes) may be a chronic, lifelong metabolic disease (or condition) in which a patient's body is unable to produce any or enough insulin, or is unable to use the insulin it does produce (insulin resistance), leading to elevated levels of glucose in the patient's blood. The three most identifiable types of diagnosed diabetes include: pre-diabetes, type 1 diabetes, and type 2 diabetes. Pre-diabetes is a condition in which blood sugar is high, but not high enough to be type 2 diabetes. Type 2 diabetes is a chronic condition that affects the way the body processes blood sugar. Lastly, type 1 diabetes is a chronic condition in which the pancreas produces little or no insulin.

Diabetes generally is diagnosed in several ways. Diagnosing diabetes may require repeated testing on multiple days to confirm the positive diagnosis of a types of diabetes. Some health parameters that doctors or other suitable healthcare providers use when confirming a diabetes diagnosis include glycated hemoglobin (A1C) levels in the blood, fasting plasma glucose (FPG) levels, oral glucose tolerance tests, and/or random plasma glucose tests. Commonly, a healthcare provider is interested in a patient's A1C level to assist in the diagnosis of diabetes. Glycated hemoglobin is a form of hemoglobin that is measured primarily to identify the three-month average plasma glucose concentration that may be used by doctors and/or other suitable healthcare providers include weight, age, nutritional intake, exercise activity, cholesterol levels, triglyceride levels, obesity, tobacco use, and family history.

Once a diagnosis of a type of diabetes is confirmed by a doctor or other suitable healthcare provider, the patient may undergo treatment to manage their diabetes. Patients having their diabetes tracked or monitored by a doctor or other healthcare provider may be treated by a combination of controlling their blood sugar through diet, exercise, oral medications, and/or insulin treatment. Regular screening for complications is also required for some patients. Depending on how long a patient has been diagnosed with diabetes, mHealth application 1 may suggest a specific treatment plan to manage their condition(s). Oral medications typically include pills taken by mouth to decrease the production of glucose by the liver and make muscle more sensitive to insulin. In other instances, where the diabetes is more severe, additional medication may be required for treating the patient's diabetes, including injections. An injection of basal insulin, also known as background insulin, may be used by healthcare providers to keep blood glucose levels at consistent levels during periods of fasting. When fasting, the patient's body steadily releases glucose into the blood to supply the cells with energy. An injection of basal insulin is therefore needed to keep blood glucose levels under control, and to allow the cells to take in glucose for energy. Basal insulin is usually taken once or twice a day depending on the type of insulin. Basal insulin acts over a relatively long period of time and therefore is considered long acting insulin or intermediate insulin. In contrast, a bolus insulin may be used to act quickly. For example, a bolus of insulin that may be specifically taken at meal times to keep blood glucose levels under control following a meal. In some instances, when a doctor or healthcare provider generates a treatment plan to manage a patient's diabetes, the doctor creates a basal-bolus dose regimen involving, e.g., taking a number of injections throughout the day. A basal-bolus regimen, which may include an injection at each meal, attempts to roughly emulate how a non-diabetic person's body delivers insulin. A basal-bolus regimen may be applicable to people with type 1 and type 2 diabetes. In addition to the basal-bolus regimen requiring injections of insulin, the treatment plan may be augmented with the use of prescribed oral medications. A patient's adherence to a treatment plan may be important in managing the disease state of the patient. In instances where the patient has been diagnosed with diabetes for more than six months, for example, a very specific treatment regimen must be followed by the patient to achieve healthy, or favorable, levels of blood glucose. Ultimately, weekly patterns of these medication types of treatments may be important in managing diabetes. mHealth application 1 may recommend treatment plans to help patients manage their diabetes.

Exemplary Methods

As applied herein, a digital therapeutic is an evidence-based therapeutic intervention implemented using one or more software programs to prevent, manage, or treat a medical disorder or disease. As an example, the mHealth application 1 of FIG. 1 is a digital therapeutic intervention. A digital therapeutic may rely on implementing behavioral and/or lifestyle changes which may be prompted by one or more collection of digital impetuses. As a result of the digital nature of digital therapeutics, data can be collected and/or analyzed for improving the digital therapeutic, improving propagation of the digital therapeutic, improving or implementing reporting based on the use of the digital therapeutic, or improving patient care.

Techniques disclosed herein may be used to improve a current digital therapeutic implementation state given that digital therapeutics are part of a new industry with noisy or conflicting information, having uncertain implementation models, unsettled nomenclature, a lack of measurements or metrics, unique implementations, a lack of stability, and/or a lack of points of comparison. Implementations may be used to standardized nomenclature, process configurations, apply configuration stability, broad applicability (e.g., multi disease/domain), and allows measurements and benchmarking.

A digital therapeutic, such as the mHealth application 1, may be implemented as a treatment or therapy that utilizes digital data, sensors, user data, user background information, disease data, medical information, or the like to encourage or cause a change in a user's actions, behavior, and/or habits. According to an implementation, a digital therapeutic may itself provide a treatment via an electronic device 19. For example, a digital therapeutic application (e.g., mHealth application 1) may output a digital treatment using an electronic device 19. The digital treatment may be an auditory treatment, visual treatment, olfactory treatment, haptic treatment, or a combination thereof or the like. The digital treatment may be output using one or more components of the electronic device 19 such as, but not limited to a speaker, a screen, a projector, a olfactory component, a haptic component, or any other applicable component that is part of or may be connected to (e.g., wired connect, wireless connection, etc.) an electronic device 19 associated with the digital therapeutic.

A digital therapeutic may be used as a preventive measure for patients who are at risk of developing and/or worsening medical conditions. For example, a user with prediabetes may be prescribed a digital therapeutic to change the user's diet and behavior that may otherwise lead to a diabetes diagnosis. A digital therapeutic can also be used as a treatment option for existing conditions. For example, a patient with type II diabetes may use a digital therapeutic to manage the disease more effectively based on a treatment plan implemented using the digital therapeutic (e.g., mHealth application 1), as disclosed herein. The digital therapeutic may be used to alert, guide, or encourage the user regarding medication, exercise, diet, and/or one or more other aspects of disease management.

According to an implementation of the disclosed subject matter, a digital therapeutic may be implemented using an electronic device 19 and/or server 29 that may obtain initial data from a user 8 or about a user before generating a digital treatment plan. The user 8 may enter the data into the electronic device 19, which may be sent to server 29. In some examples, server 29 may receive data that is relevant to a healthcare provider, e.g., a doctor may enter related patient healthcare information into server 29. This data may be electronically transmitted by the provider and/or the user 8 and received by the server 29. The data may be electronically transmitted and received by the server 29 in any suitable manner. For example, the provider may access a digital therapeutic application (e.g., mHealth application 1) or secure server and send or drop electronic data files via a network so that the files may be accessed by the digital therapeutic application. In some examples, the provider may allow the digital therapeutic application limited access, in compliance with any healthcare privacy regulations and other applicable regulations, to any electronic medical records, user prescription records, referral records, etc. In some examples, the service may electronically retrieve healthcare data from such electronic records (e.g., automatically). In other examples, user data may be electronically transmitted by a user 8 and may be electronically received by the service in any suitable manner. The user data may be manually input by the user 8 via the digital therapeutic application and/or may be automatically retrieved by the service from an electronic device of the user (e.g., electronic device 19) that may measure user health values, such as heart rate, blood glucose, blood oxygen, blood pressure, activity, stress, mood, and/or sleep either periodically or continuously. In some examples, the user 8 may be required to complete a questionnaire and/or survey. The questionnaire may be presented to the user 8 during a setup of the digital therapeutic application.

In another example, initial data may be received from other application software downloaded to a device 19 (e.g., an application on a smart phone corresponding to a fitness band tracker used to collect data on calories burned, steps walked, or the like, by the user 8). This initial data may be collected from the other application software either periodically or continuously over a period of time.

The data received by the server may be stored in a database (e.g., database 302 of FIG. 3). The data may be accessed at any time and may be displayed, printed, or updated in any suitable manner. The stored data may be organized and accessed in any suitable manner. In some examples, the data may be electronically tagged with various identifiers, such as age, gender, clinical condition, etc.

The initial data may include an identification of one or more disease states of the user 8 and/or other parameters associated with the health of the user 8. For example, initial data may include a diagnosis of diabetes selected from the following types: type 1, type 2, pre-diabetes, gestational diabetes, early on-set diabetes, late adult on-set diabetes, etc. Initial data may include blood glucose level, hemoglobin A1C level, blood pressure value, low-density lipid level, high-density lipid level, triglyceride cholesterol level, total cholesterol level, body mass index (BMI), age, weight, tobacco use, alcohol use, exercise activity (e.g., step count, calories burned, heart rate), and stage of diabetes/severity of disease. Other types of data also may be included. In some examples, the initial data may include a length of time that the user 8 has been diagnosed with a disease, such as, e.g., diabetes. The initial data also may include other relevant data of the user 8, including a clinical profile of the user 8 such as history of diseases, significant medical events (e.g., heart attack, stroke, head trauma, transplant), lab values, user self-reported clinical, behavioral and psycho-social data, user's demographics, medical history. In one example, when the disease is diabetes, relevant data of the user may be clinical data of the user since the original diagnosis, and also may include clinical data of the user from before the original diagnosis. In this example, if the user 8 has had type-2 diabetes for the 20 years, the relevant historical data may include at least the user's A1C levels and/or blood glucose levels during those 20 years. Other suitable data sets that may be collected include metabolic data (e.g., blood pressure, blood glucose, weight, LDL, lab results, and the like), medication (e.g., dose, frequency, class of medication), symptoms (e.g., structured and unstructured inputs), diet (e.g., food, calories, protein, fat, carbohydrates, sodium, allergies, and the like), activity (e.g., type, duration, intensity, and the like), and psycho-social (e.g., financial, claims, beliefs, barriers, and the like).

For any data collected from the user 8, metadata may be extracted from the stored data. In some other examples, the system, the device, and/or the server may suggest places to eat based on geo-tagging results of the user 8 (e.g., provide the user 8 with recommendations for restaurants in proximity to the user 8 with healthy menu options). In some examples, based on geo-tagged restaurants, restaurant menu data can be extracted, and healthier menu options from the menu data can be presented to the user 8 (e.g., menu items containing low sugar or no sugar can be presented to the user). In some examples, restaurant meal data may be entered into server 29 and/or device 19 by the user 8. In both examples, meal options may be presented to the user 8 based on the restaurant meal data based on, for example, time of day, information on the user's eating habits, user personal preferences, medications, and/or exercise.

Initial data also may include medications the user 8 is currently taking (e.g., oral medications, basal injections and/or bolus injections) and data related to the user's health and lifestyle, such as, e.g., adherence history to prescribed medication (e.g., glycemic, oral insulin, etc.), adherence history to prescribed medication dosage (e.g., glycemic, oral insulin, etc.) correlated to its effect on said blood glucose level, carbohydrate intake, weight, psycho-social determinants, and blood glucose level testing frequency correlated to its effect on said blood glucose level. In some examples, a user's history of engagement frequency with the electronic device 19 also may be used in the initial user data. For example, the digital therapeutic application may generate a more complex digital treatment plan if the user 8 shows a high engagement frequency with electronic device 19. The initial data also may include data input by a healthcare provider, and may include subjective opinions of the user 8 by the healthcare provider. For example, the data may include the healthcare provider's subjective opinions regarding the user's motivation, compliance, overall health, and the like. The digital therapeutic application may weigh the subjective opinions of the provider when creating a treatment plan. For example, if the provider's subjective opinion of the user 8 is that the user 8 has a high compliance to medication and dietary regimens, but a low compliance to exercise regimens, then a subsequent treatment plan generated by mHealth application 1 may include a larger emphasis on medication and diet, as opposed to exercise. Additionally, mHealth application 1 also may use this information to focus tutorials and educational content sent to the user 8 on exercise topics and the benefits of exercise relative to the user's health.

The server 29 may associate the user 8 with a cohort of other users (e.g., a group of users having similar physical, medical, psycho-determinant conditions) based on similarities between the user 8 and other users. For example, a male having a height of 70 inches, weighing 190 pounds, and having high blood pressure, Indian ethnicity, type-2 diabetes, and an A1C level of approximately 6.8%, may be associated with users of a cohort having similar characteristics. As previously disclosed, a user 8 with an A1C level of greater than 6.5% is considered diabetic. A cohort, in this example, could be a group of Indian American males having similar blood pressures, heights, weights, and A1C levels that have responded well to a particular treatment plan and/or responded poorly to other plans. For example, a group of males of Indian ethnicity, 68-72 inches tall, weighing 175-200 pounds, may respond well to an oral medication treatment for type-1 diabetes if the medication is taken twice daily at a particular dosage and time schedule. As set forth below, goals and/or treatment plans may be assigned to the user 8 based on the association with the cohort based on results or goals/treatments of the users within the cohort. A doctor or other suitable healthcare provider, or the digital therapeutic application itself, may establish a goal and/or treatment plan based on goals and/or treatment plans that were successful within the cohort to treat a specific medical condition. In some examples, a cohort may include a small number of users, e.g., two users, while in other examples, a cohort may include more users, e.g., dozens, hundreds, or thousands. Depending on the specific medical condition or chronic disease, the doctor or other suitable healthcare provider wishes to address, the cohort may change.

The digital therapeutic application may receive one or more goals from the user 8 or other suitable healthcare provider, or mHealth application 1 may generate a goal based on the initial data received. In other examples, the goal may be a default goal, such as, e.g., lowering blood glucose levels of the user 8 when the application is a blood glucose management application. The goal may include improving one or more health parameters of the user, such as, e.g., blood glucose level, hemoglobin A1C level, blood pressure, low-density lipid level, high-density lipid level, triglyceride cholesterol level, total cholesterol level, body mass index (BMI), weight, user activity level, sleep duration, sleep quality, adherence to prescribed medication, nutrition (e.g., carbohydrate intake), psycho-social determinants, and blood glucose level testing frequency correlated to its effect on said blood glucose level, among others. The goal may be determined by mHealth application 1 based on the previously entered information, including information based on the user's disease state, history of user's disease, and/or other initial user data. The goal also may be determined based on the cohort associated with the user 8. One or more machine learning algorithms may be used by the server 29 to help determine the goal. In some examples, goal may include a time period after which the goal should be achieved. For example, the goal may be to lower a user's A1C level by a certain amount over a fixed time period (e.g., a treatment window to alleviate a specific health parameter of the user 8). In some examples, the fixed time period may be one day, one week, one year, or any other suitable time period. In some examples, the time period may be expanded or reduced by mHealth application 1 based on the user's progress or compliance over the course of the time period. For example, mHealth application 1 may reduce a fixed treatment window from 20 weeks to 16 weeks if the user's A1C levels are responding to a specific treatment earlier than anticipated.

The goal also may include multiple parameters that should be improved over the course of the treatment window. For example, a user 8 may set a goal of losing 10 pounds and to drop her A1C level from 6.7% to 6.3% over a 12 week time period. In another example, the digital therapeutic application may set a goal to reduce the user's total cholesterol level over a 20 week time period, in addition to reducing their blood pressure to a normal level, e.g., 120/80 mm Hg from an elevated level. In this example, the digital therapeutic application may expand the 20 week window if the user is not on track to meet their goal over the original 20 week window. For example, at week 15, the digital therapeutic application may increase the time period for the user 8 to reach their goal to 30 weeks if the health parameter is determined to be unattainable within the original time period.

Figure 4:
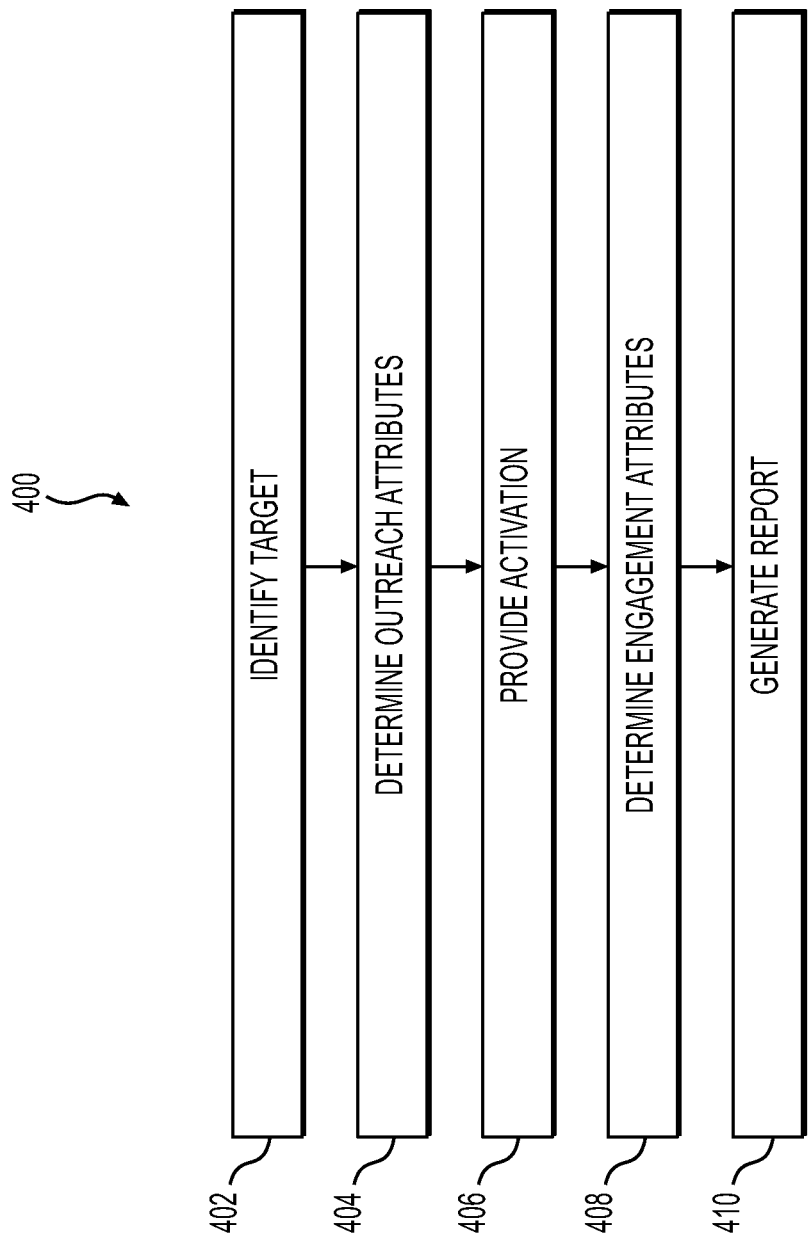
FIG. 4 is a flowchart of a digital therapeutic method, according to an example of the present disclosure.

According to implementations, a digital therapeutics experience chain is disclosed for optimizing the adoption of digital therapeutic solutions in one or more populations and/or patient cohorts. FIG. 4 is a flow diagram of an exemplary method 400 for implementing a digital therapeutics experience chain. In some examples, the depicted method 400 may be used to implement adoption of a digital therapeutic by a patient population. The method 400 provides, but is not limited to, a set of macro-level processes that characterize the enterprise and end-user consumption experience with a digital therapeutic. Method 400 provides a framework to establish a common vernacular, measures to characterize a digital therapeutic implementation experience, benchmark and quantification of performance at one or more stages, and the like. All or parts of the method 400 may be configured to optimize a portion of the digital therapeutic implementation experience via one or more environments or entities (e.g., a hospital system, health insurer, self-insured individual, employer, etc.). As disclosed herein, outputs associated with the one or more stages of method 400 may be used to improve the digital therapeutic implementation such as by comparing experience performance within similar or different environments or entities.

Figure 5:
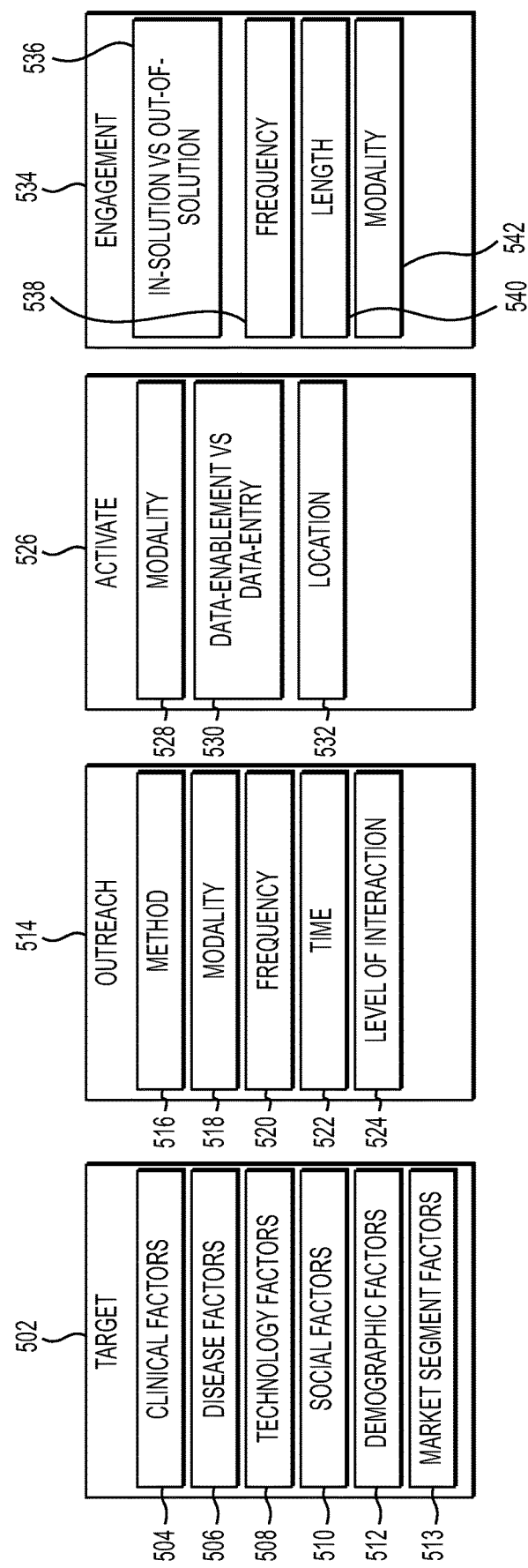
FIG. 5 is a plurality of stage based flowcharts, according to an example of the present disclosure.

As shown in FIG. 4, at stage 402, one or more targets may be identified. The one or more targets may be individuals, groups, or entities that are candidates for a given digital therapeutic solution or generally to digital therapeutic solutions. For simplicity, this disclosure may generally refer to targets as individuals. The one or more targets may be identified based on one or more of clinical factors, disease factors, technology or technography factors, social factors, and/or demographic factors. At stage 404, one or more outreach attributes may be determined. The outreach attributes may be techniques, systems, devices, or implementations for reaching all or a portion of the targets identified at stage 402. The one or more outreach attributes may be determined based on one or more of a method, a modality, a frequency, a time, a level of interaction, or the like. At stage 406, one or more activations may be provided for activating the digital therapeutic for which targets are identified at stage 402. The activations may be implemented via techniques, systems, devices, or the like for activating the one or more targets such that the one or more targets use the digital therapeutic or digital therapeutics in general. The activations may be determined based on one or more of a modality, a data-enablement verses data entry, and/or a location, or the like. At stage 408, one or more engagement attributes may be determined. The engagement attributes may be associated with improving the engagement of the digital therapeutic by one or more targets identified at stage 402. The engagement attributes may be determined using one or more of an in-solution verses an out-of-solution engagement, frequency, length, and/or modality of engagement, or the like. FIG. 5 shows each of the factors and their respective components. At stage 410, a report based on any one or more of the stages 402, 404, 406, or 408 may be generated.

The digital therapeutic experience chain of method 400 provides a set of macro-level processes that characterize the enterprise and end-user consumption experience with a digital therapeutic. It provides a framework to establish a common vernacular, definitions, and measures that can be used to characterize the experience and bencher/qualify performance at different points throughout the experience. All or a portion of the digital therapeutic experience chain of method 400 may be used as a configurator to optimize the experience in different operating environment (e.g., hospital system, health insurer, self-insured employer, etc.). All or a portion of the digital therapeutic experience chain of method 400 may be used to drive continuous improvement by comparing experience performance with similar environments and across different environments.

At stage 402, one or more targets may be identified based on a determination of one or more ideal candidates for a given digital therapeutic (e.g., the mHealth application 1) solution or for digital therapeutic solutions in general. The targets may be a subset of end-users that offer an optimal opportunity to demonstrate success with use of the digital therapeutic. The targets may be identified based on attributes of the targets and/or based on attributes of a given digital therapeutic. For example, if the deployment of a given digital therapeutic is not implementable by a given target (e.g., if the target does not have a specific electronic device to implement the digital therapeutic), then even if that target is likely to use the digital therapeutic, the target may not be an identified target. Additionally, according to an implementation, a potential target's feedback potential may be considered when identifying the one or more targets. For example, a potential target that provides an ability to measure primary parameters required to determine successful deployment of the digital therapeutic may be identified over a potential target that does not.

The identified targets may be individuals, groups, or entities that are likely to use a given digital therapeutic or those who may benefit from the use of the given digital therapeutic. For example, the identified targets may be individuals who are more likely than one or more other individuals to use the digital therapeutic application, based on information obtained regarding each of the individuals. As another example, the identified targets may be individuals with a medical condition (e.g., pre-diabetes, high blood pressure, high cholesterol, diabetes, hypertension, obesity, other heart disease, etc.) that may benefit from the digital therapeutic (e.g., a diabetes centric digital therapeutic such as mHealth application 1). The targets may be identified based on one or more factors, as shown in the target section 502 of FIG. 5 including, but not limited to, clinical factors 504, disease factors 506, technology or technography factors 508, social factors 510, demographic factors 512 (e.g., geographic factors), and/or a market segment factors 513.

Clinical factors 504 may include, but are not limited to, users with different health acuity based on key clinical markers. The markers may include, for example, HbA1c for diabetes, blood pressure for hyper tension, weight/height for obesity, cholesterol levels for heart disease, patient attributes for corresponding conditions, test results for corresponding conditions, or the like. The clinical factors 504 may indicate the severity of a medical condition or may be used to indicate the potential for a user with a given medical condition to use a given digital therapeutic. For example, a group of pre-diabetic individuals may be identified as targets for the mHealth application 1 based on the likelihood that the individuals can benefit from the mHealth application.

Clinical factors 504 may be obtained from accessing a cloud database via network 32, where the database may store clinical factors 504 associated with a plurality of potential targets. Clinical factors 504 may be input by the potential targets using, for example, respective electronic devices 19. Clinical factors 504 may be correlated with a plurality of potential targets (e.g., while maintaining the respective potential target's identity hidden). The correlation may be made using diagnosis, medical conditions, and/or electronic medical record (EMR) data and correlating the same with the potential targets (e.g., patient ID, EMR ID, etc.). Clinical factors 504 may be obtained from health care providers or systems (e.g., doctors, hospital networks, EMRs, etc.) via network 32.

Disease factors 506 may allow targeting users with different co-morbid conditions. For example, a targeted user may be an individual who has hypertension and congestive heart failure or an individual who has diabetes or heart disease. Users with multiple disease factors 506 may be more likely to use a digital therapeutic as, for example, using a digital therapeutic instead of or in conjunction with traditional medication may improve their individual treatment plans. As an example, a digital therapeutic may be used in conjunction with traditional medication to, at least in part, alert a patient regarding the timings of medicine consumption. A user with comorbid conditions may rely on the digital therapeutic as it may be too difficult to ensure medicine compliance without the digital therapeutic. Clinical factors and/or disease factors 506 may be based on metabolic conditions, medicine regimen driven, and/or co-morbidity driven.

Disease factors 506 may be obtained from accessing a cloud database via network 32, where the database may store disease attributes associated with a plurality of potential targets. Disease factors 506 may be input by the potential targets using, for example, respective electronic devices 19. Disease factors 506 may be correlated with a plurality of potential targets (e.g., while maintaining the respective potential target's identity hidden). The correlation may be made using diagnosis, medical conditions, and/or electronic medical record (EMR) data and correlating the same with the potential targets (e.g., patient ID, EMR ID, etc.). Disease factors 506 may be obtained from health care providers or systems (e.g., doctors, hospital networks, EMRs, etc.) via network 32.

Technology or technography factors 508 may allow targeting users with different levels of technological sophistication or different types of access to technology. Technological sophistication may correspond to one or more of experience with technology in general, experience with a specific technology associated with a given digital therapeutic, proficiency with technology, comfort level using technology (e.g., general or specific), indicated preference regarding technology, or the like. Access to technology may include access to a network (e.g., wired or wireless internet connection) and/or access to hardware (e.g., connected medical devices, wearables, mobile devices, computers, laptops, tablets, IoT sensors, etc.).

Technology or technography factors 508 may be obtained based on assessing a user's technological sophistication based on observing an interaction of a given user with a given technological device (e.g., electronic device 19) or technological interface. The assessment may be based on a user initiated session, based on data received from a third party, or based on real-time or recorded interactions of the user. Technology or technography factors 508 may be input by the potential targets using, for example, respective electronic devices 19. For example, a user may input their comfort level using a mobile device or a wearable device. Technology or technography factors 508 may be determined by accessing a database (e.g., via network 32) to determine the types of devices associated with a user or user account. For example, a user account may consolidate information about each of the user's devices and the user account may be accessed to determine the user's access to technology. Technology or technography factors 508 may be determined based on a user's purchase history. For example, a user may purchase a medical device and that transaction may be recorded and obtained to determine that the user is able to use the given medical device.

Social factors 510 may allow targeting patients with different social determinants or constraints, such as levels of education, income, access to care, mental health (e.g., anxiety, depression, distress, etc.) or the like. Social factors 510 may determine the likelihood of a potential target using a digital therapeutic. For example, a user that relies on their mobile device to cope with a mental health condition may be more likely to use a digital therapeutic while a user with ample access to care may opt to elect the care over a digital therapeutic.

Social factors 510 may be obtained by accessing a cloud database via network 32, where the database may store social attributes associated with a plurality of potential targets. Social factors 510 may be input by the potential targets using, for example, respective electronic devices 19. Social factors 510 may be correlated with a plurality of potential targets (e.g., while maintaining the respective potential target's identity hidden). The correlation may be made using electronic medical record (EMR) data and correlating the same with the potential targets (e.g., patient ID, EMR ID, etc.). Social factors 510 may be obtained from health care providers or systems (e.g., doctors, hospital networks, EMRs, etc.) via network 32 and/or via social networks associated with the potential targets.

Demographic factors may allow targeting patients with different demographic attributes such as geography (e.g., city, state, country, region, terrain) age, rural or urban denomination, or the like. Demographic factors may determine the likelihood of a potential target using a digital therapeutic based on, for example, data associated with other individuals from the same or similar demographic indicating whether those other individuals use digital therapeutics. For example, the country of a potential target may be used to determine if the potential target is likely to use a digital therapeutic based on use of digital therapeutics by other individuals form the same country.

Demographic factors may be obtained by accessing a cloud database via network 32, where the database may store demographic attributes associated with a plurality of potential targets. Demographic factors may be input by the potential targets using, for example, respective electronic devices 19. Demographic factors may be correlated with a plurality of potential targets (e.g., while maintaining the respective potential target's identity hidden). The correlation may be made using electronic medical record (EMR) data, survey data, and/or record data, and correlating the same with the potential targets (e.g., patient ID, EMR ID, etc.). Demographic factors may be obtained from health care providers or systems (e.g., doctors, hospital networks, EMRs, etc.) via network 32 and/or social networks associated with the potential targets.

A market segment based factors 513 may allow targeting patients based on access to care based on different market providers. The market segments may include private insurance, commercial insurance, Medicare, Medicaid, concierge coverage, or the like. Market segment factors 513 may indicate whether a potential target user is likely to use a digital therapeutic. For example, it may be determined that users that are covered using commercial insurance are more likely to use digital therapeutics. Market segment information may be obtained by accessing a cloud database via network 32, where the database may store insurance attributes associated with a plurality of potential targets. Market segment factors 513 may be input by the potential targets using, for example, respective electronic devices 19. Market segment factors 513 may be correlated with a plurality of potential targets (e.g., while maintaining the respective potential target's identity hidden). The correlation may be made using electronic medical record (EMR) data, survey data, and/or record data, and correlating the same with the potential targets (e.g., patient ID, EMR ID, etc.). Market segment factors 513 may be obtained from health care providers or systems (e.g., doctors, hospital networks, EMRs, etc.) via network 32.

Accordingly, at stage 402, a plurality of targets may be identified based on one or more of the factors disclosed above. The plurality of targets may be identified based on a likelihood that the identified plurality of targets are more likely than others to use a given digital therapeutic or digital therapeutics in general. The identified plurality of targets may be stored locally or in a cloud database such as one or more servers 29 via network 32.

At stage 404, one or more outreach attributes 514, as shown in FIG. 5, may be identified based on a determination of how best to increase awareness of a given digital therapeutic (e.g., the mHealth application 1) solution. The outreach attributes 514 may include services, methodology, individuals, groups, or entities that are likely to promote use of a given digital therapeutic. For example, the outreach attributes 514 may identify individuals who are more often in contact with targets that are likely to use the given digital therapeutic. The outreach attributes 514 may be identified based on one or more factors including, but not limited to, methods 516, modalities 518, frequency 520, time 522, and/or level of interaction. The outreach attributes 514 may determine how to most effectively reach the identified targets to use a digital therapeutic. The number of iterations of outreach (e.g., number of campaigns, touch points, etc.) may be a factor when determining outreach attributes.

Additionally, a scalability potential may be considered when determining outreach attributes 514. The scalability potential may account for increased reach and/or cost-effectiveness of outreach.

The method 516 of outreach may be an attribute that dictates the propagation of a given digital therapeutic. A first digital therapeutic may be propagated faster using a first method of outreach whereas a second digital therapeutic may be propagated faster using a second method of outreach. The methods 516 of outreach may include, but are not limited to, human outreach, automated outreach, or the like. Human outreach may include prescription based outreach such as from a physician, or may include an incentive or information sharing via an individual such as a doctor, health care professional (e.g., a registered dietitian (RD), clinical dietary educator (CDE), social worker (SW), etc.), user of a digital therapeutic, or the like. Automated outreach may be conducted using one or more technological modalities and may be broadcast, multicast, or may be used to reach one target user at a time.

The modality 518 of the outreach may be in-person, via technology, via one or more communication modes, or the like. Examples of modalities 518 include, but are not limited to digital advertising, email, website, portal access, messages, social media promotions, telephone calls, chat sessions, social gatherings, in-person discussions, or the like. Physical outreach may be conducted via on premise promotion, mail promotions, or the like.

The frequency 520 of outreach may be determined to optimize the propagation of a given digital therapeutic. For example, a balance ratio may be determined for the amount of outreach over a given amount of time such that a target user is not oversaturated by the outreach but is provided enough touch points for the outreach to be effective. A comprehensive outreach implementation may include varying the frequency 520 of outreach per method 516 and/or per modality 518 such that a first method of outreach may be more frequent than a second method of outreach. The frequency 520 may be determined based on an output of a machine learning model that inputs, for example, target user attributes, clinical factors 504, disease factors 506, technology factors 508, social factors 510, demographic factors 512, and/or market segment factors 513 to output a frequency 520. Machine learning models that may be used are discussed further herein. The frequency 520 may be based on a user action such as a user receipt of a given promotion via a given modality 518 and a subsequent use or non-use of a digital therapeutic. For example, if a user sees a promotional outreach and does not use given digital therapeutic, then a frequency of the promotional outreach or a different promotional outreach may be adjusted based on the user not using the given digital therapeutic.

The time 522 of outreach may be determined to optimize the propagation of a given digital therapeutic. For example, one or more optimal times to reach a target user may be determined such that the one or more optimal times correspond to times when the target user is most likely to use the digital therapeutic. The time 522 of outreach may be user specific, a target factor specific, or may be general and apply to a group or all target users. A comprehensive outreach implementation may include varying the time 522 of outreach per method 516 and/or per modality 518 such that a first method of outreach may be used at a first time and a second method of outreach may be used at a second time. The time 522 may be determined based on an output of a machine learning model that inputs, for example, target user attributes, clinical factors 504, disease factors 506, technology factors 508, social factors 510, demographic factors 512, and/or market segment factors 513 to output a time 522. Machine learning models that may be used are discussed further herein. The time 522 may be based on a user action such as a user receipt of a given promotion via a given modality 518 and a subsequent use or non-use of a digital therapeutic. For example, if a user sees a promotional outreach at a first time and does not use given digital therapeutic, then a time 22 of the promotional outreach may be adjusted based on the user not using the given digital therapeutic.

A level of interaction 524 may be determined to optimize the propagation of a given digital therapeutic. The level of interaction 524 may be a categorization of interaction such as a one-way interaction or a two-way (i.e., interactive) interaction. Alternatively, or in addition, the level of interaction 524 may include a duration, depth, or extent of interaction. For example, a human interaction may be two minutes long or fifteen minutes long. However, it may be determined that an outreach greater than three minutes provides diminishing returns. Accordingly, the level of interaction 524 may be capped at three minutes to prevent over-saturating a target user. The level of interaction 524 may be determined based on an output of a machine learning model that inputs, for example, target user attributes, clinical factors 504, disease factors 506, technology factors 508, social factors 510, demographic factors 512, and/or market segment factors 513 to output a level of interaction 524. Machine learning models that may be used are discussed further herein.

At stage 406, one or more activations 526, of FIG. 5, may be provided based on a determination of how best to activate a digital therapeutic (e.g., the mHealth application 1) solution for one or more target users. The activation 526 may be based on one or more of a modality 528, data-enablement verses data-entry 530, and/or location 532 and may be human-assisted (e.g., at a clinic or office, via human communication, remote assisted, tele-assisted, etc.), technology driven (e.g., via a mobile application, electronic prompts, etc.) and/or automated via technology (e.g., via a non-deep link, deep link, automated bot, etc.). The provided activation 526 may be selected to maximize an activation to outreach ratio such that the provided activation 526 is most effective given one or more corresponding outreach attributes 514.

The modality 518 of the activation may be assisted, self-activated, or the like. Examples of modalities 518 include, a user self activating the digital therapeutic, the user receiving guidance via a technological platform (e.g., email, messaging, application portal, social media portal, guided or automated chats, etc.), telephone calls, or the like. For example, a user may receive a link at a given time 522 such that the selection of the link results in activation of the digital therapeutic. As another example, a user may receive a phone call from an automated system to remind the user to activate the digital therapeutic at a given time. According to an implementation, users may be able to select their preferred modality based on one or more modality options. According to another implementation, the modality 518 may be determined based on an output of a machine learning model that inputs, for example, target user attributes, clinical factors 504, disease factors 506, technology factors 508, social factors 510, demographic factors 512, and/or market segment factors 513 to output a modality 518. Machine learning models that may be used are discussed further herein.

Data-enablement verses data-entry 530 may refer to the pre-population of data verses a user entry of data. A determination may be made regarding the lack of activation based on the amount of data a user may need to enter. Accordingly, available data may be pulled from one or more devices and/or systems including, but not limited to, electronic devices 19, EMR 14, pharmacy 9, servers 29, or the like and may be received via network 32. The data enablement may be based on the target user attributes, clinical factors 504, disease factors 506, technology factors 508, social factors 510, demographic factors 512, market segment factors 513 to output a modality 518, electronic devices 19, prior user inputs, and/or the like.

Activation may be provided based on location 532 which may be any applicable location that a digital therapeutic can be activated. Location 532 may be a doctor's office, heath care provider location, home, work, or the like. The location 532 may be a location that changes from a first activation to a second activation. Further, location 532 for a single activation may vary such as, for example, if a user activates a given digital therapeutic while traveling or commuting.

At 408, one or more engagement attributes may be determined. The engagement attributes may be determined to maximize engagement with the digital therapeutic or based on the digital therapeutic. Engagement based on the digital therapeutic may be different than engagement with the digital therapeutic such that engagement based on the digital therapeutic may utilize tools, processes, techniques, etc. outside an application associated with the digital therapeutic. For example, a digital therapeutic application may determine an optimal time for a user to take glucose medication. However, instead of or in addition to alerting a user to take the glucose medication at the optimal time, the digital therapeutic may cause an SMS message to be sent to the user's phone. Accordingly, the engagement with the SMS message may be based on the digital therapeutic. As shown in FIG. 5, the engagement attributes 534 may be based on in-solution (e.g., within a digital therapeutic application) verses out-of-solution 536. The one or more engagement attributes may be based on identifying which subsets of users exhibit common engagement patterns and further based on what defines these patterns (e.g., demographics, drug regimens, use of specific in-application features, etc.). The engagement attributes may be based utilizing health care professionals to optimize engagement by users with a given digital therapeutic (e.g., in a manner that is easy to use, manageable, fits into workflow, etc.). Engagement attributes may define or may be selected based on engagement metrics that provide feedback regarding a given engagement.

Engagement attributes 534 may further be based on a frequency 538 of engagement, length 540 of engagement, and/or modality 542 of engagement. As examples, engagement be via a software application related to the digital therapeutic (e.g., guided data collection, real-time feedback (RTFB), longitudinal feedback (LFB), insights, education, support, comprehensive data analysis (CDA), Artificial Intelligence, etc.), via a prescribing healthcare provider (e.g., that may order use of the digital therapeutic, review clinical decision support or clinical decision system (CDS), adjust the digital therapeutic plan, etc.), via a care team or program administrator (e.g., individual intervention, population intervention, etc.), via customer care (e.g., onboarding, human engagement, trouble management, prescription upgrades, etc.), via an artificial intelligence engine (e.g., human analytics and intervention, automated analytics and intervention, etc.), or the like.

A frequency 538 of engagement may be the amount of times a digital therapeutic is engaged in a given amount of time. The frequency 538 may be optimized to balance a necessity (e.g., medical compliance, exercise compliance, dietary compliance, etc.) with engagement saturation. The frequency 538 may be individual based or may be based on a group or all users. A length 540 of engagement may be the duration of an engagement and/or the duration of an activity, or task conducted based on an engagement. The length 540 may be optimized to promote use of the digital therapeutic as necessitated by a given user's conditions or needs. The modality 542 of engagement or treatment may be any applicable medium such as an application, webpage, software, wearable device, mobile device, holographic device, telephone, virtual reality (VR) system, augmented reality system (AR), or the like.

At stage 410, a report may be generated. The report may be based on any data related to stages 402, 404, 406, and 408 of method 400 of FIG. 4, as disclosed herein. The report may include one or more components of enrollment for a given digital therapeutic, outcomes from one or more stages of method 400, or the like. For example, the report may include one or more of cost metrics, effectiveness metrics, time metrics, individual cost metrics, population based cost metrics, individual effectiveness metrics, population based effectiveness metrics, individual time metrics, population based time metrics, or the like. According to an implementation, the report may impute a value to the integrated approach to implementing a digital therapeutic solution via method 400. The report may identify where integration should occur (e.g., at one or more stages of method 400) within a digital therapeutic experience chain (e.g., method 400) as well as one or more sources or components of value that the integration contributes.

The report may be generated in any applicable format such that it usable by a human user (e.g., a screen, a webpage, application, PDF, excel, text based report, or the like) or by an automated system (e.g., a feedback loop, a machine learning model, etc.). The report may provide one or more of an informative analysis (e.g., based on information received from a patient or health care system), discovery analysis (e.g., based on items discovered during implementation of method 400), extrapolative analysis (e.g., identification of potential changes), adaptive analysis (e.g., results from implementing one or more changes), or the like. The report may be provided such that it is organized, searchable, and/or filterable. For example, the report may be filterable to by one or more of the factors or attributes shown in FIG. 5 (e.g., clinical factors 504, method of outreach 514, modality 528 of activation, frequency 538 of engagement, etc.).

The report may be generated to identify the most useful data to improve or validate a digital therapeutic experience chain, as shown via the stages in method 400. For example, for a first stage or subsequent stage, the report may show relevant data associated with that stage and/or data that would allow improvement of that stage. For example, the report may include data used to identify targets at stage 402 and may use the activation data from stage 406 to provide insight about the targets at stage 402. The report may be generated by using the available data to discover trends, patterns, and/or insights. The report may identify practices and/or policies to be put into place to meet good data science governance policies.

Figure 6:
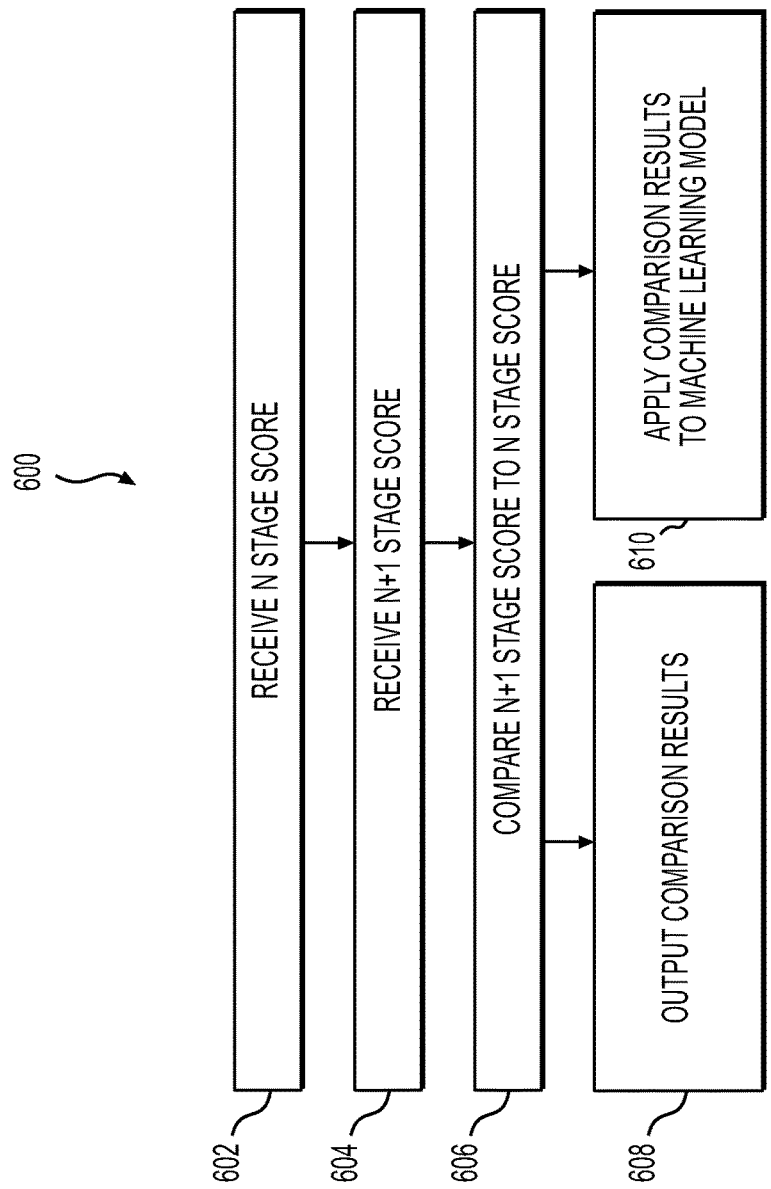
FIG. 6 flowchart for generating comparison results, according to an example of the present disclosure.

FIG. 6 shows a method 600 for outputting comparison results from two or more stages of method 400 and applying the comparison results to a machine learning model. As disclosed herein, the comparison results may be include in the report generated at stage 410 of method 400.

At step 602, an N stage score may be received. An N stage may correspond to any one of the stages 402, 404, 406, 408, or 410 of method 400. An N stage score may correspond to a score associated with implementation of the respective stage. The N stage score may be based on the success of that given stage as determined on stage specific factors. The success of a given stage may be based on predetermined or dynamically determined criteria or may be based on comparison to previous iterations of a given stage. As examples, stage 402 may include target identification factors (e.g., number of targets identified, ratio of targets identified, comparison of targets identified with previously identified targets, etc.), stage 404 may include outreach factors (e.g., click-through rates, view rates, user involvement rates, percentage of targets reached, etc.), stage 406 may include activation based factors (e.g., frequency of activation, percentage of users that activated the digital therapeutic in a given amount of time, cause of activation, consistency of activation, etc.), stage 408 may include engagement based factors (e.g., duration of engagement, quality of engagement, frequency of engagement, result from engagement, etc.). At 604 an N+1 stage score may be received. The N+1 stage may correspond to a stage subsequent to the N stage at step 602. For example, if the N stage score is from stage 402, then the N+1 stage score corresponds to a score for stage 404.

At 606, the N+1 stage score may be compared to the N stage score. The comparison may be any applicable comparison such as a ratio between the N stage score and the N+1 stage score, a difference between the N stage score and the N+1 stage score, a change in the N stage score vs a change in the N+1 stage score or the like. The comparison may be a number, a ranking, a designation, a fraction, or the like. The comparison of the N+1 stage score to the N stage score may provide insight into one or both of the stages. For example, if the N stage score is disproportionately higher than the N+1 stage score (e.g., as indicated by a ratio), then the difference may trigger an adjustment to the N+1 stage. As a specific example if, at stage 402, the score associated with identifying targets is 100 but the outreach, at stage 404, to those targets is 20, this may indicate a large discrepancy between stage 402 and 404. Accordingly, as a result, one or more changes may be triggered. For example, during a subsequent iteration, more resources may be expended for the outreach stage 404 in comparison to the target identification stage 402.

At 608, the comparison results may be output. The output may be part of a report, generated at stage 410 of method 400 or may be output independently of a report. The comparison results may be output via any applicable format (e.g., a screen, a webpage, application, PDF, excel, text based report, or the like). The comparison result may be output into an input component of a digital therapeutic system such that a change to one or more of the stages of method 400 is implemented based on the comparison result.

Figure 7:
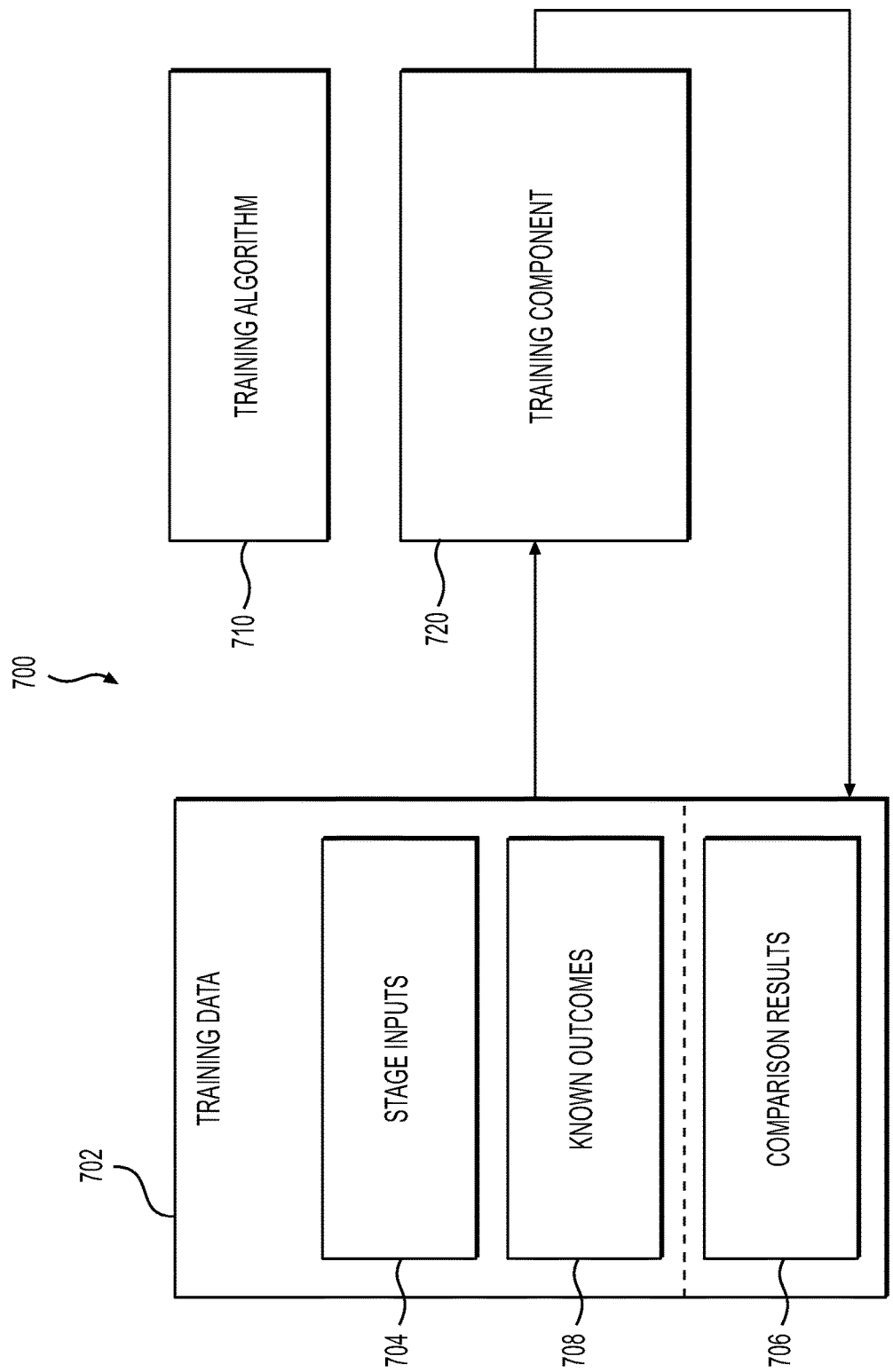
FIG. 7 flowchart for training a machine learning model, according to an example of the present disclosure.

Alternatively, or additionally, at 610, a comparison result may be applied to a machine learning model. The comparison result may be the input or may be one of the inputs to the machine learning model such that a change to one or more of the stages of method 400 is implemented based on the comparison result based machine learning model output. FIG. 7 shows a comparison result 706 component, as further disclosed herein.

One or more of the stages of method 400, factors or attributes of FIG. 5, and/or comparisons of method 600 may be implemented based on the output of one or more machine learning models. For simplicity, a single machine learning model will be discussed herein but it will be understood that multiple machine learning models may be used for respective different outputs. A machine learning model may be trained using a dataset including supervised, partially supervised, or unsupervised sample digital therapeutic data (e.g., from actual or simulated stages of method 400). For example, a learning algorithm or network (e.g., clustering algorithm, a neural network, a deep learning network, a genetic learning algorithm, or algorithms based on Convolutional Neural Networks (CNN), CNN with multiple-instance learning or multi-label multiple instance learning, Recurrent Neural Networks (RNN), Long-short term memory RNN (LSTM), Gated Recurrent Unit RNN (GRU), graph convolution networks, etc.) may be provided digital therapeutic data. By applying a large plurality of such digital therapeutic data, the machine learning algorithm may be used to train a machine learning model provides applicable outputs (e.g., targets, outreach attributes, activations, engagement attributes, reports, one or more factors or attributes from FIG. 5, etc.).

FIG. 7 shows an example training module 700 to train a digital therapeutic system machine learning model. As shown in FIG. 7, training data 702 may include one or more of stage inputs 704 (e.g., one or more outputs from a stage from method 400, a factor or attribute from FIG. 5, etc.), and known outcomes 708 (i.e., known or desired outputs for future inputs similar to or in the same category as stage inputs 704 that do not have corresponding known outputs) related to a digital therapeutic system. The training data 702 and a training algorithm 710 may be provided to a training component 720 that may apply the training data 702 to the training algorithm 710 in order to generate a digital therapeutic machine learning model. According to an implementation, the training component 720 may be provided comparison results from step 610 of method 600. The comparison result may be used by the training component 720 to update the digital therapeutic machine learning model. For example, a ratio of stage 404 compared to stage 402 may be used to modify the digital therapeutic machine learning model such that it favors outreach over target identification for a subsequent iteration of the method 400.

Figure 8:
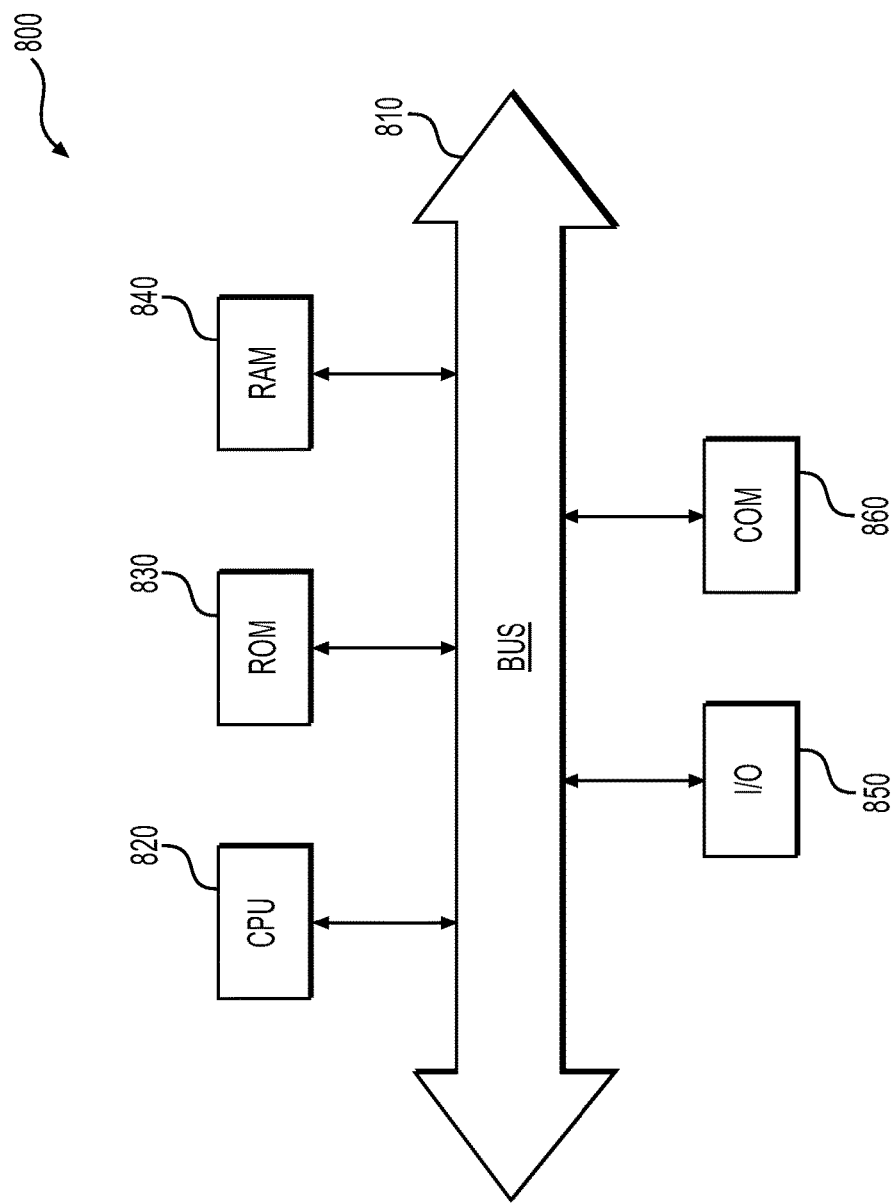
FIG. 8 is a simplified functional block diagram of a computer that may be configured as a host server, for example, to function as healthcare provider decision-making server, according to an example of the present disclosure.

FIG. 8 is a simplified functional block diagram of a computer that may be configured as a host server, for example, to function as healthcare provider decision-making server. FIG. 8 illustrates a network or host computer platform 800. It is believed that those skilled in the art are familiar with the structure, programming, and general operation of such computer equipment and as a result, the drawings should be self-explanatory.

A platform for a server 800 or the like, for example, may include a data communication interface for packet data communication 860. The platform also may include a central processing unit (CPU) 820, in the form of one or more processors, for executing program instructions. The platform typically includes an internal communication bus 810, program storage, and data storage for various data files to be processed and/or communicated by the platform such as ROM 830 and RAM 840 or the like. The hardware elements, operating systems, and programming languages of such equipment are conventional in nature, and it is presumed that those skilled in the art are adequately familiar therewith. The server 800 also may include input and output ports 850 to connect with input and output devices such as keyboards, mice, touchscreens, monitors, displays, etc., and communication ports 860. Of course, the various server functions may be implemented in a distributed fashion on a number of similar platforms to distribute the processing load. Alternatively, the servers may be implemented by appropriate programming of one computer hardware platform.

The report or any applicable output may further identify the relative value that one or more points of integration provide. For example, potential points of integration may include program integration (e.g., providing an organized structure around implementation of a digital therapeutic solution), health care provider integration (e.g., engaging a clinical key entity at various points in a digital therapeutic experience chain), system or EMR integration (e.g., reducing friction in ease of provider interactions as well as data accessibility with the digital therapeutic).

Figure 9:
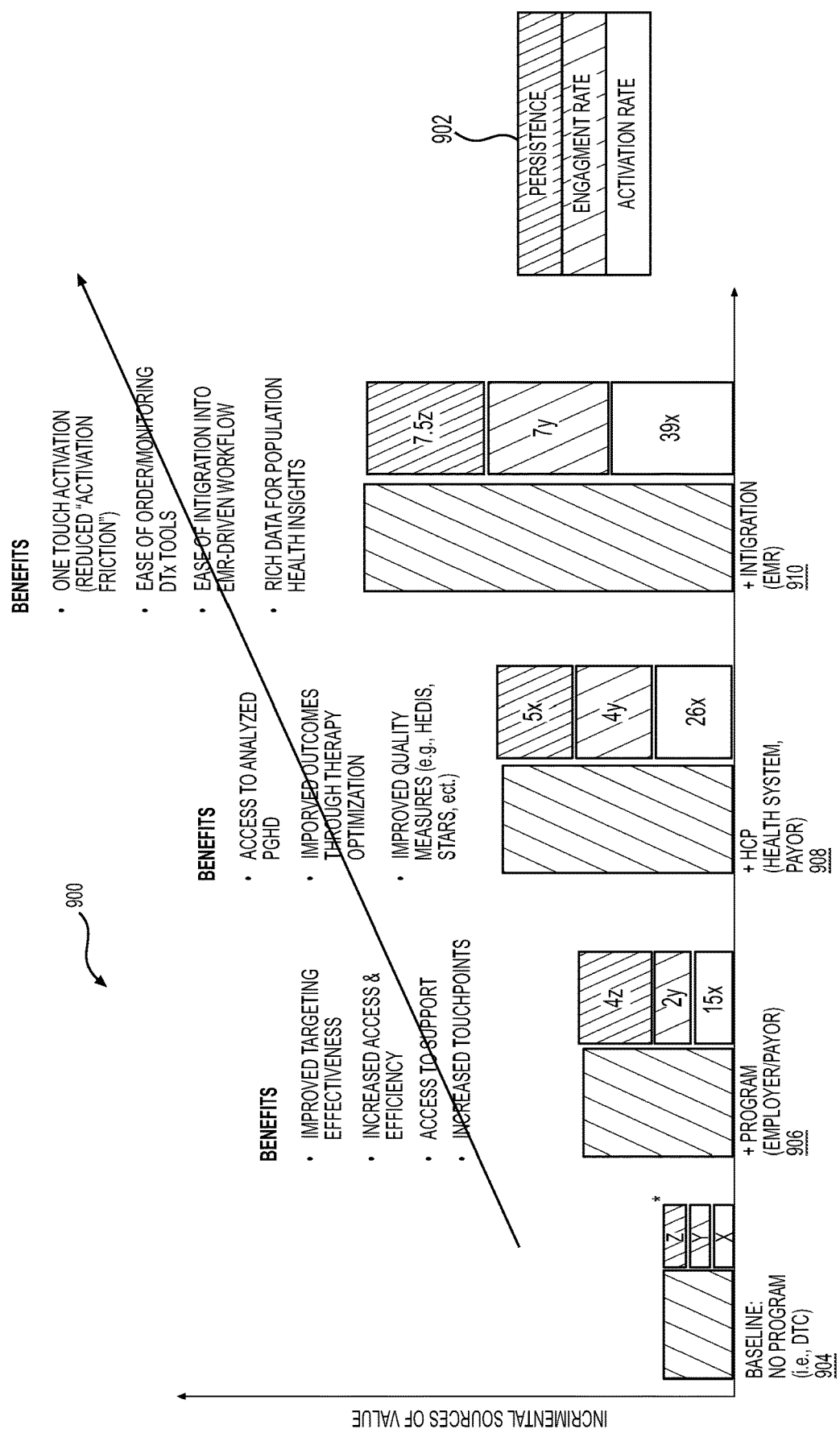
FIG. 9 is a chart showing experimental results, according to an example of the present disclosure.

Experimental results have shown that an incremental effect on key digital therapeutic metrics sources of value, as provided in chart 900 of FIG. 9. As shown in legend 902, persistence is indicated by a dot pattern, engagement rate is indicated by a check pattern, and an activation rate is indicated by a solid shape. As shown, in comparison to a baseline 904 of having a direct to consumer implementation (i.e., no digital therapeutic experience chain such as method 400), a program that includes involvement by an employer or payer at 906 shows improved training effectiveness, increased access and efficiency, access to support, and increased touchpoints. In this scenario, persistence increased by 4×, engagement by 2×, and activation rate by 15×. As shown, in comparison to a baseline 904 of having a direct to consumer implementation with an incremental program that includes involvement by an employer or payer at 906, a program that involved a healthcare provider (e.g., health system, payer) shows improved access to analyzed patient-generated health data (PGHD), improved outcomes through therapy optimization, improved quality measures (e.g., Centers for Medicare & Medicate Services (CMS)Health Effectiveness Data and Information Set (HEIS), CMS Star Rating, etc.). In this scenario, persistence increased by 5×, engagement by 4×, and activation rate by 26×. As shown, in comparison to a baseline 904 with an incremental program that includes involvement by an employer or payer at 906, and an incremental program that involved a healthcare provider (e.g., health system, payer) at 908, a program that ads integration (e.g., EMR integration) shows one touch activation (e.g., reduce activation friction), ease of order, monitoring of digital therapeutic tools, ease of integration into EMR driven workflow, rich data for population health insights. In this scenario, persistence increased by 7.5×, engagement by 7×, and activation rate by 39×.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

It would be apparent to one of skill in the relevant art that the present disclosure, as described herein, can be implemented in many different examples of software, hardware, firmware, and/or the entities illustrated in the figures. Any actual software code with the specialized control of hardware to implement examples is not limiting of the detailed description. Thus, the operational behavior of examples will be described with the understanding that modifications and variations of the examples are possible, given the level of detail presented herein.

It is to be understood that both the foregoing general description and the following detailed description are exemplary and explanatory only and are not restrictive of the disclosed examples, as claimed.

Other examples of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for deploying a digital therapeutic program, the method comprising:

determining a likelihood of use of the digital therapeutic for each of a plurality of users, wherein a machine learning model receives a plurality of user characteristics to output the likelihood of use of the digital therapeutic for each of the plurality of users, wherein each of the plurality of users can access the digital therapeutic using a single respective account linked to one or more respective target user electronic devices, wherein the digital therapeutic for a given user from the plurality of users communicates with at least one external application associated with the given user, the external application selected from at least one of an exercise tracking application or a health related application, each respective target user electronic device configured to received data from a clinical data server and a user interface server, the user interface server configured to receive and process user inputs, each respective target user electronic device comprising a presentation layer selected from a web browser, application, or messaging interface, wherein the presentation layer provides notifications and alerts associated with the digital therapeutic, wherein the digital therapeutic is configured to output a treatment based on:

initial data comprising current medication, adherence history to prescribed medications, carbohydrate intake, weight, and blood glucose levels;

a user history of engagement with a respective target user electronic device; and an identified cohort of users associated with each of the plurality of users, respectively, the identified cohort of users determined based on one of a similarity in physical condition, similarity in medical condition, or similarity in psycho determinant condition;

determining a feedback potential for each of the plurality of users, the feedback potential corresponding to a likelihood of feedback of the digital therapeutic, wherein the machine learning model outputs the feedback potential based the user characteristics, past feedback potentials, and past user characteristics;

identifying a plurality of target users from the plurality of users for the digital therapeutic based on one or more target parameters comprising the likelihood of use of the digital therapeutic and the feedback potential for each of the plurality of target users and further based on at least one clinical factor wherein a clinical factor is based on a health acuity, at least one disease factor, wherein the at least one disease factor is based on a presence of a co-morbid condition, at least one social factor, wherein the at least one social factor is based on one or more of a level of education, an income, an access to care, or mental health, and at least one geographical factor, wherein the at least one geographical factor is based on one or more of a geographical attribute and an age attribute;

determining access to technology for each of the plurality of users, the access to technology comprising identifying access to a wired or wireless internet connection and access to hardware, the hardware comprising a respective target user electronic device that is connected to the wired or wireless internet connection;

determining a technological sophistication for each of the plurality of users, the technological sophistication being determined based on an interaction with the respective target user electronic device, the interaction being assessed real-time;

determining a market segment factor for each of the plurality of users, the market segment factor comprising a likelihood of insurance coverage for each respective plurality of users, the market segment factor being based on market segment information received from a cloud database that comprises insurance attributes associated with the each of the plurality of users;

identifying the plurality of target users further based on the access to technology for each of the plurality of users, and excluding the plurality of users for whom the access to technology is not sufficient;

identifying the plurality of users further based on the technological sophistication for each of the plurality of users, and excluding the plurality of users for whom the technological sophistication is not sufficient;

identifying the plurality of users further based on the market segment factor and excluding the plurality of users for whom the market segment factor indicates a low likelihood of insurance coverage;

identifying optimal outreach for one or more of the plurality of target users using an outreach medium, wherein the optimal outreach is provided to a highest awareness output selected from one or more of a service output, a methodology output, an individual output, a group output, or an entity output, wherein the outreach is identified based on an outreach factor selected from one or more of an outreach method, an outreach modality, an outreach frequency, an outreach time, and an outreach level of interaction the outreach medium being conducted based on a scalability potential, wherein:

the outreach method is an automated outreach, the outreach modality is a technological modality selected from a broadcast, a multicast or a single cast modality, and the outreach frequency is based on a balance ratio determined based on an amount of outreach over an outreach time period, the ratio output by the machine learning model to prevent oversaturation;

identifying an activation to optimize use of the digital therapeutic using respective target user electronic devices wherein the machine learning model identifies the activation based the user characteristics, past activation, and past characteristics, the activation based on one or more of a modality, a data-enablement verses data-entry, or location, the activation being identified to maximize an activation to outreach ratio, the activation being automated via at least one of a non-deep link, deep link, or automated bot;

providing medical treatments via the digital therapeutic on respective target user electronic devices, based on importing activity tracking device data for the respective target users, the medical treatments comprising a specific treatment plan, the specific treatment plan comprising a medication component, a diet component, and an exercise component;

receiving an engagement level of the digital therapeutic by one or more of the plurality of target users via the target user electronic devices, wherein the engagement level comprises a frequency of engagement determine based on an amount of times the digital therapeutic is engaged with by the one or more of the plurality of users and further comprises a length of engagement based on a duration of engagement with the digital therapeutic by the one or more plurality of users; and updating the machine learning model based on the received engagement level and further by a training component based on a comparison result of the plurality of target users to a number of user reached via the optimal outreach.

2. The computer-implemented method of claim 1, further comprising generating a report based on one or more of the target users, the outreach, the activation, or activating the digital therapeutic.

3. The computer-implemented method of claim 2, wherein the report is based on one or more of an informative analysis, discovery analysis, extrapolative analysis, or an adaptive analysis.

4. The computer-implemented method of claim 2, wherein the report comprises a comparison of an N+1 stage score to an N stage score for each stage except a final stage.

5. The computer-implemented method of claim 1, wherein the activation is based on one or more of a modality, data-enablement verses data-entry, or a location.

6. The computer-implemented method of claim 1, wherein the engagement level is based on one or more of an in-solution versus out-of-solution, a frequency, a length, or a modality, wherein the in-solution corresponds to the digital therapeutic and the out-of-solution is external to the digital therapeutic.

7. The computer-implemented method of claim 1, wherein at least one of the identifying the plurality of target users, conducting outreach, identifying an activation, and activating the activation is based on an output of a machine learning model.

8. The computer-implemented method of claim 7, wherein the machine learning model is trained using training data that comprises one or more of stage inputs, known outcomes, and comparison results.

9. The computer-implemented method of claim 8, wherein the comparison results are a ratio of an N+1 stage score to an N stage score for each stage except a final stage.

10. A system for deploying a digital therapeutic, the system comprising:

a data storage device storing a machine learning model, wherein the machine learning model is trained using at least one of supervised training or unsupervised training; and a processor operatively connected to the data storage device and configured to execute the machine learning model for:

determining a likelihood of use of the digital therapeutic for each of a plurality of users, wherein the machine learning model receives a plurality of user characteristics to output the likelihood of use of the digital therapeutic for each of the plurality of users, wherein each of the plurality of users can access the digital therapeutic using a single respective account linked to one or more respective target user electronic devices, wherein the digital therapeutic for a given user from the plurality of users communicates with at least one external application associated with the given user, the external application selected from at least one of an exercise tracking application or a health related application, each respective target user electronic device configured to received data from a clinical data server and a user interface server, the user interface server configured to receive and process user inputs, each respective target user electronic device comprising a presentation layer selected from a web browser, application, or messaging interface, wherein the presentation layer provides notifications and alerts associated with the digital therapeutic, wherein the digital therapeutic is configured to output a treatment based on:

initial data comprising current medication, adherence history to prescribed medications, carbohydrate intake, weight, and blood glucose levels;

a user history of engagement with a respective target user electronic device; and an identified cohort of users associated with each of the plurality of users, respectively, the identified cohort of users determined based on one of a similarity in physical condition, similarity in medical condition, or similarity in psycho determinant condition;

determining a feedback potential for each of the plurality of users, the feedback potential corresponding to a likelihood of feedback of the digital therapeutic, wherein the machine learning model outputs the feedback potential based the user characteristics, past feedback potentials, and past user characteristics;

identifying a plurality of target users from the plurality of users for the digital therapeutic based on one or more target parameters comprising the likelihood of use of the digital therapeutic and the feedback potential for each of the plurality of target users and further based on at least one clinical factor wherein a clinical factor is based on a health acuity, at least one disease factor, wherein the at least one disease factor is based on a presence of a co-morbid condition, at least one social factor, wherein the at least one social factor is based on one or more of a level of education, an income, an access to care, or mental health, and at least one geographical factor, wherein the at least one geographical factor is based on one or more of a geographical attribute and an age attribute;

determining access to technology for each of the plurality of users, the access to technology comprising identifying access to a wired or wireless internet connection and access to hardware, the hardware comprising a respective target user electronic device that is connected to the wired or wireless internet connection;

determining a technological sophistication for each of the plurality of users, the technological sophistication being determined based on an interaction with the respective target user electronic device, the interaction being assessed real-time;

determining a market segment factor for each of the plurality of users, the market segment factor comprising a likelihood of insurance coverage for each respective plurality of users, the market segment factor being based on market segment information received from a cloud database that comprises insurance attributes associated with the each of the plurality of users;

identifying the plurality of target users further based on the access to technology for each of the plurality of users, and excluding the plurality of users for whom the access to technology is not sufficient;

identifying the plurality of users further based on the technological sophistication for each of the plurality of users, and excluding the plurality of users for whom the technological sophistication is not sufficient;

identifying the plurality of users further based on the market segment factor and excluding the plurality of users for whom the market segment factor indicates a low likelihood of insurance coverage;

identifying optimal outreach for one or more of the plurality of target users using an outreach medium, wherein the optimal outreach is provided to a highest awareness output selected from one or more of a service output, a methodology output, an individual output, a group output, or an entity output, wherein the outreach is identified based on an outreach factor selected from one or more of an outreach method, an outreach modality, an outreach frequency, an outreach time, and an outreach level of interaction the outreach medium being conducted based on a scalability potential, wherein:

the outreach method is an automated outreach, the outreach modality is a technological modality selected from a broadcast, a multicast or a single cast modality, and the outreach frequency is based on a balance ratio determined based on an amount of outreach over an outreach time period, the ratio output by the machine learning model to prevent oversaturation;

identifying an activation to optimize use of the digital therapeutic using respective target user electronic devices wherein the machine learning model identifies the activation based the user characteristics, past activation, and past characteristics, the activation based on one or more of a modality, a data-enablement verses data-entry, or location, the activation being identified to maximize an activation to outreach ratio, the activation being automated via at least one of a non-deep link, deep link, or automated bot;

providing medical treatments via the digital therapeutic on respective target user electronic devices, based on importing activity tracking device data for the respective target users, the medical treatments comprising a specific treatment plan, the specific treatment plan comprising a medication component, a diet component, and an exercise component;

receiving an engagement level of the digital therapeutic by one or more of the plurality of target users via the target user electronic devices, wherein the engagement level comprises a frequency of engagement determine based on an amount of times the digital therapeutic is engaged with by the one or more of the plurality of users and further comprises a length of engagement based on a duration of engagement with the digital therapeutic by the one or more plurality of users; and updating the machine learning model based on the received engagement level and further by a training component based on a comparison result of the plurality of target users to a number of user reached via the optimal outreach.

11. The system of claim 10, wherein the one or more target parameter is identified based on one or more of attributes of the target users or attributes of the digital therapeutic.

12. The system of claim 10, wherein the one or more target parameters comprises a market segment based factor, wherein the market segment based factor is selected from one or more of a private insurance, a commercial insurance, Medicare, Medicaid, or a concierge coverage.

13. The system of claim 10, further comprising generating a report based on one or more of cost metrics, effectiveness metrics, time metrics, individual cost metrics, population based cost metrics, individual effectiveness metrics, population based effectiveness metrics, individual time metrics, population based time metrics, the feedback potential, the target parameters, or the outreach.

14. The system of claim 10, wherein the machine learning model is further trained my modifying one of one or more weights or one or more layers based on training data.

15. A non-transitory computer-readable medium storing instructions that, when executed by processor, cause the processor to perform operations for deploying a digital therapeutic program, the operations comprising:

determining a likelihood of use of the digital therapeutic for each of a plurality of users, wherein a machine learning model receives a plurality of user characteristics to output the likelihood of use of the digital therapeutic for each of the plurality of users, wherein each of the plurality of users can access the digital therapeutic using a single respective account linked to one or more respective target user electronic devices, wherein the digital therapeutic for a given user from the plurality of users communicates with at least one external application associated with the given user, the external application selected from at least one of an exercise tracking application or a health related application, each respective target user electronic device configured to received data from a clinical data server and a user interface server, the user interface server configured to receive and process user inputs, each respective target user electronic device comprising a presentation layer selected from a web browser, application, or messaging interface, wherein the presentation layer provides notifications and alerts associated with the digital therapeutic, wherein the digital therapeutic is configured to output a treatment based on:

initial data comprising current medication, adherence history to prescribed medications, carbohydrate intake, weight, and blood glucose levels;

a user history of engagement with a respective target user electronic device; and an identified cohort of users associated with each of the plurality of users, respectively, the identified cohort of users determined based on one of a similarity in physical condition, similarity in medical condition, or similarity in psycho determinant condition;

determining a feedback potential for each of the plurality of users, the feedback potential corresponding to a likelihood of feedback of the digital therapeutic, wherein the machine learning model outputs the feedback potential based the user characteristics, past feedback potentials, and past user characteristics;

identifying a plurality of target users from the plurality of users for the digital therapeutic based on one or more target parameters comprising the likelihood of use of the digital therapeutic and the feedback potential for each of the plurality of target users and further based on at least one clinical factor wherein a clinical factor is based on a health acuity, at least one disease factor, wherein the at least one disease factor is based on a presence of a co-morbid condition, at least one social factor, wherein the at least one social factor is based on one or more of a level of education, an income, an access to care, or mental health, and at least one geographical factor, wherein the at least one geographical factor is based on one or more of a geographical attribute and an age attribute;

determining access to technology for each of the plurality of users, the access to technology comprising identifying access to a wired or wireless internet connection and access to hardware, the hardware comprising a respective target user electronic device that is connected to the wired or wireless internet connection;

determining a technological sophistication for each of the plurality of users, the technological sophistication being determined based on an interaction with the respective target user electronic device, the interaction being assessed real-time;

determining a market segment factor for each of the plurality of users, the market segment factor comprising a likelihood of insurance coverage for each respective plurality of users, the market segment factor being based on market segment information received from a cloud database that comprises insurance attributes associated with the each of the plurality of users;

identifying the plurality of target users further based on the access to technology for each of the plurality of users, and excluding the plurality of users for whom the access to technology is not sufficient;

identifying the plurality of users further based on the technological sophistication for each of the plurality of users, and excluding the plurality of users for whom the technological sophistication is not sufficient;

identifying the plurality of users further based on the market segment factor and excluding the plurality of users for whom the market segment factor indicates a low likelihood of insurance coverage;

identifying optimal outreach for one or more of the plurality of target users using an outreach medium, wherein the optimal outreach is provided to a highest awareness output selected from one or more of a service output, a methodology output, an individual output, a group output, or an entity output, wherein the outreach is identified based on an outreach factor selected from one or more of an outreach method, an outreach modality, an outreach frequency, an outreach time, and an outreach level of interaction the outreach medium being conducted based on a scalability potential, wherein:

the outreach method is an automated outreach, the outreach modality is a technological modality selected from a broadcast, a multicast or a single cast modality, and the outreach frequency is based on a balance ratio determined based on an amount of outreach over an outreach time period, the ratio output by the machine learning model to prevent oversaturation;

identifying an activation to optimize use of the digital therapeutic using respective target user electronic devices wherein the machine learning model identifies the activation based the user characteristics, past activation, and past characteristics, the activation based on one or more of a modality, a data-enablement verses data-entry, or location, the activation being identified to maximize an activation to outreach ratio, the activation being automated via at least one of a non-deep link, deep link, or automated bot;

providing medical treatments via the digital therapeutic on respective target user electronic devices, based on importing activity tracking device data for the respective target users, the medical treatments comprising a specific treatment plan, the specific treatment plan comprising a medication component, a diet component, and an exercise component;

receiving an engagement level of the digital therapeutic by one or more of the plurality of target users via the target user electronic devices, wherein the engagement level comprises a frequency of engagement determine based on an amount of times the digital therapeutic is engaged with by the one or more of the plurality of users and further comprises a length of engagement based on a duration of engagement with the digital therapeutic by the one or more plurality of users; and updating the machine learning model based on the received engagement level and further by a training component based on a comparison result of the plurality of target users to a number of user reached via the optimal outreach.

16. The non-transitory computer-readable medium of claim 15, further comprising generating a report based on one or more of the target users, the outreach, the activation, or activating the digital therapeutic.

17. The non-transitory computer-readable medium of claim 16, wherein the report comprises a comparison of an N+1 stage score to an N stage score for each stage except a final stage.

* * * * *